(12) United States Patent
Stancer et al.

(10) Patent No.: US 8,929,995 B2
(45) Date of Patent: Jan. 6, 2015

(54) IMPLANTABLE MEDICAL DEVICE TELEMETRY IN DISRUPTIVE ENERGY FIELD

(75) Inventors: Christopher C. Stancer, Prescott, WI (US); Volkert A. Zeijlemaker, Landgraaf (NL)

(73) Assignee: Medtronic, Inc., Minneapolis, MN (US)

( * ) Notice: Subject to any disclaimer, the term of this patent is extended or adjusted under 35 U.S.C. 154(b) by 1045 days.

(21) Appl. No.: 12/916,074

(22) Filed: Oct. 29, 2010

(65) Prior Publication Data

US 2012/0109260 A1     May 3, 2012

(51) Int. Cl.
*A61N 1/08* (2006.01)
*A61N 1/37* (2006.01)
*A61N 1/39* (2006.01)
*A61N 1/372* (2006.01)

(52) U.S. Cl.
CPC .............. *A61N 1/3718* (2013.01); *A61N 1/3925* (2013.01); *A61N 1/37252* (2013.01)
USPC ........................................................ 607/60

(58) Field of Classification Search
CPC ....... A61N 1/37; A61N 1/3718; A61N 1/372; A61N 1/37252; A61N 1/39; A61N 1/08; A61N 2001/086
USPC ................ 607/59–60, 63; 600/411, 422–423; 128/899
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,190,034 A | 3/1993 | Sholder | |
| 5,545,186 A | 8/1996 | Olson et al. | |
| 5,755,736 A | 5/1998 | Gillberg et al. | |
| 7,050,855 B2 | 5/2006 | Zeijlemaker et al. | |
| 7,561,915 B1 | 7/2009 | Cooke et al. | |

(Continued)

FOREIGN PATENT DOCUMENTS

WO     2007/134143 A2     11/2007

OTHER PUBLICATIONS

International Search Report and Written Opinion of international application No. PCT/US2011/034558, dated Aug. 5, 2011, 14 pp.

(Continued)

*Primary Examiner* — Carl H Layno
*Assistant Examiner* — Jessica Anthony
(74) *Attorney, Agent, or Firm* — Michael J. Ostrom; Stephen W. Bauer

(57) ABSTRACT

An implantable medical device may include a telemetry module, a sensing module, a therapy delivery module, and a processor. The processor may be configured to detect a patient event based on data generated by the sensing module, operate the IMD in a first mode in which the telemetry module is disabled and the therapy delivery module is at least partially disabled when the patient event is not detected, and operate the IMD in a second mode in which the telemetry module is enabled and the therapy delivery module is at least partially disabled when the patient event is detected. In some examples, the processor is configured to, in the second mode, generate a notification of the cardiac arrhythmia and transmit the notification to an external device via the telemetry module. The external device may reside inside an MRI room or outside the MRI room, and may communicate with other devices.

32 Claims, 12 Drawing Sheets

(56) References Cited

U.S. PATENT DOCUMENTS

| | | |
|---|---|---|
| 7,623,930 B2 | 11/2009 | Zeijlemaker et al. |
| 7,660,620 B2 | 2/2010 | Zeijlemaker et al. |
| 2005/0070975 A1 | 3/2005 | Zeijlemaker et al. |
| 2006/0025820 A1 | 2/2006 | Phillips et al. |
| 2006/0167496 A1 | 7/2006 | Nelson et al. |
| 2006/0241392 A1 | 10/2006 | Feinstein et al. |
| 2006/0293591 A1 | 12/2006 | Wahlstrand et al. |
| 2007/0238975 A1 | 10/2007 | Zeijlemaker |
| 2007/0265685 A1 | 11/2007 | Zeijlemaker |
| 2010/0023084 A1 | 1/2010 | Gunderson |
| 2010/0211123 A1 | 8/2010 | Stubbs et al. |
| 2011/0093046 A1* | 4/2011 | Ellingson et al. .............. 607/60 |
| 2012/0229299 A1* | 9/2012 | Skoldengen et al. .... 340/870.02 |

OTHER PUBLICATIONS

International Preliminary Report on Patentability from corresponding PCT Application Serial No. PCT/US2011/034558 dated Jan. 29, 2013 (15 pages).

Reply to Written Opinion from corresponding PCT Application Serial No. PCT/US2011/034558 dated Jan. 8, 2013 (6 pages).

Reply to Written Opinion from corresponding PCT Application Serial No. PCT/US2011/034558 dated Apr. 27, 2012 (14 pages).

Written Opinion of the International Preliminary Examining Authority for international application No. PCT/US2011/034558, dated Nov. 20, 2012, 9 pp.

* cited by examiner

IMPLANTABLE MEDICAL DEVICE TELEMETRY IN DISRUPTIVE ENERGY FIELD

TECHNICAL FIELD

The disclosure relates to implantable medical devices (IMDs) and, more particularly, to operation of IMDs exposed to a disruptive energy field.

BACKGROUND

Some types of IMDs provide therapeutic electrical stimulation to tissue of a patient via electrodes of one or more implantable leads. Examples of such IMDs include implantable cardiac pacemakers, cardioverter-defibrillators, or the like. An IMD may deliver electrical stimulation to the tissue via electrodes of implantable leads in the form of pacing stimulation, cardioversion stimulation, defibrillation stimulation, or cardiac resynchronization stimulation. In some cases, electrodes carried by the implantable leads may be used to sense one or more physiological signals to monitor the condition of a patient and/or to control delivery of therapeutic electrical stimulation based on the sensed signals.

An IMD may be exposed to an external energy field for any of a number of reasons. For example, one or more medical procedures may need to be performed on the patient within whom the IMD is implanted for purposes of diagnostics or therapy. In particular, the patient may be examined using a disruptive energy field produced, for example, by a magnetic resonance imaging (MRI) scan, computed tomography (CT) scan, or other medical procedure that produces a magnetic field, electromagnetic field, electric field or other disruptive energy field. The field may be disruptive in the sense that it may disrupt operation of the IMD in some manner.

In some examples, operation of the IMD, such as delivery of electrical stimulation by the IMD, may be impacted by a medical procedure, such as an MRI scan or CT scan. For example, a disruptive energy field may impact the ability of the IMD to deliver therapy. Also, delivery of wireless telemetry may impact the medical procedure. For example, wireless telemetry may induce noise in an MRI scan. For these reasons, it may be desirable to disable operation of the IMD during a medical procedure.

SUMMARY

In general, the disclosure is directed to devices, systems, and techniques that facilitate wireless communication between an IMD and an external receiver in the presence of a disruptive energy field, such as during an MRI scan or other medical procedure during which full operation of the IMD may be undesirable. In some examples, the devices, systems, and techniques described herein may support, in the presence of a disruptive energy field, partial functionality of the IMD, such as wireless communication to and/or from the IMD, and/or control of the IMD. The example of an MRI scan will be described for purposes of illustration, although the devices, systems, and techniques described herein may also be applicable to other disruptive energy fields, such as those generated by a CT scan or the like.

In some examples, an IMD may be programmed to operate in an MRI-compatible operating mode during an MRI scan on the patient in which the IMD is implanted. For example, the MRI-compatible operating mode may include a first mode in which the IMD can sense at least some physiological conditions of the patient, such as electrical activity of the patient's heart, and/or operational conditions of the IMD, but communication between the IMD and an external device via wireless telemetry is generally disabled. In some examples, in the MRI-compatible operating mode, the IMD also may disable delivery of at least some therapy, such as electrical cardioversion and/or defibrillation therapy. The MRI-compatible operating mode may allow the IMD to operate in a second mode in which the IMD overrides the disabling of wireless telemetry and selectively enables wireless telemetry if the IMD detects a patient event.

With selective enablement of wireless telemetry in the presence of an MRI scan, the MRI-compatible operating mode may facilitate wireless communication between the IMD and an external device when the IMD detects a patient event. In some examples, the patient event may be detected based on data generated by a sensing module, and may be related to a physiological condition, such as a cardiac arrhythmia, asystole, or the like. Other examples of patient events may include events associated with operation of the IMD, such as an operating mode of the IMD, capture or loss of capture of tissue when delivering electrical stimulation, a magnetic field sensed by a sensor of the IMD, battery status of the IMD, lead or electrical conductor conditions, or sensor operating status. In the case of a cardiac arrhythmia, asystole, or other patient event, selective enablement of telemetry may permit communication of the patient event or a notification to a caregiver, so that appropriate action, such as delivery of acute medical care, may be taken.

In one example, the disclosure describes an IMD comprising a telemetry module, a sensing module, a therapy delivery module, and a processor configured to detect a patient event based on data generated by the sensing module, operate the IMD in a first mode in which the telemetry module is disabled and the therapy delivery module is at least partially disabled when the patient event is not detected, and operate the IMD in a second mode in which the telemetry module is enabled and the therapy delivery module is at least partially disabled when the patient event is detected.

In another example, the disclosure describes a system comprising a wireless telemetry receiver antenna located within an electromagnetic interference (EMI)-shielded room, an external device communicatively coupled to the wireless telemetry receiver antenna via a wired connection, an implantable medical device (IMD) comprising a telemetry module, a sensing module, a therapy delivery module, and a processor, wherein the processor is configured to detect a patient event based on data generated by the sensing module, operate the IMD in a first mode in which the telemetry module is disabled and the therapy delivery module is at least partially disabled when the patient event is not detected, operate the IMD in a second mode in which the telemetry module is enabled and the therapy delivery module is at least partially disabled when the patient event is detected, generate a notification of the detected patient event, and transmit the notification to the external device via the telemetry module of the IMD and the wireless telemetry receiver antenna.

In a further example, the disclosure describes a method comprising detecting a patient event based on data generated by a sensing module of an implantable medical device (IMD) in a patient, operating the IMD in a first mode in which a telemetry module of the IMD is disabled and a therapy delivery module of the IMD is at least partially disabled when the patient event is not detected, and operating the IMD in a second mode in which the telemetry module is enabled and the therapy delivery module is at least partially disabled when the patient event is detected.

In an additional example, the disclosure describes a computer-readable medium comprising instructions that cause a programmable processor to detect a patient event based on data generated by a sensing module of an implantable medical device (IMD) in a patient, operate the IMD in a first mode in which a telemetry module of the IMD is disabled and a therapy delivery module of the IMD is at least partially disabled when the patient event is not detected, and operate the IMD in a second mode in which the telemetry module is enabled and the therapy delivery module is at least partially disabled when the patient event is detected.

In another example, the disclosure describes an IMD comprising means for detecting a patient event based on data generated by a sensing module of an implantable medical device (IMD) in a patient, means for operating the IMD in a first mode in which a telemetry module of the IMD is disabled and a therapy delivery module of the IMD is at least partially disabled when the patient event is not detected, and means for operating the IMD in a second mode in which the telemetry module is enabled and the therapy delivery module is at least partially disabled when the patient event is detected.

The details of one or more examples are set forth in the accompanying drawings and the description below. Other features, objects, and advantages will be apparent from the description and drawings, and from the claims.

DETAILED DESCRIPTION

Figure 1:
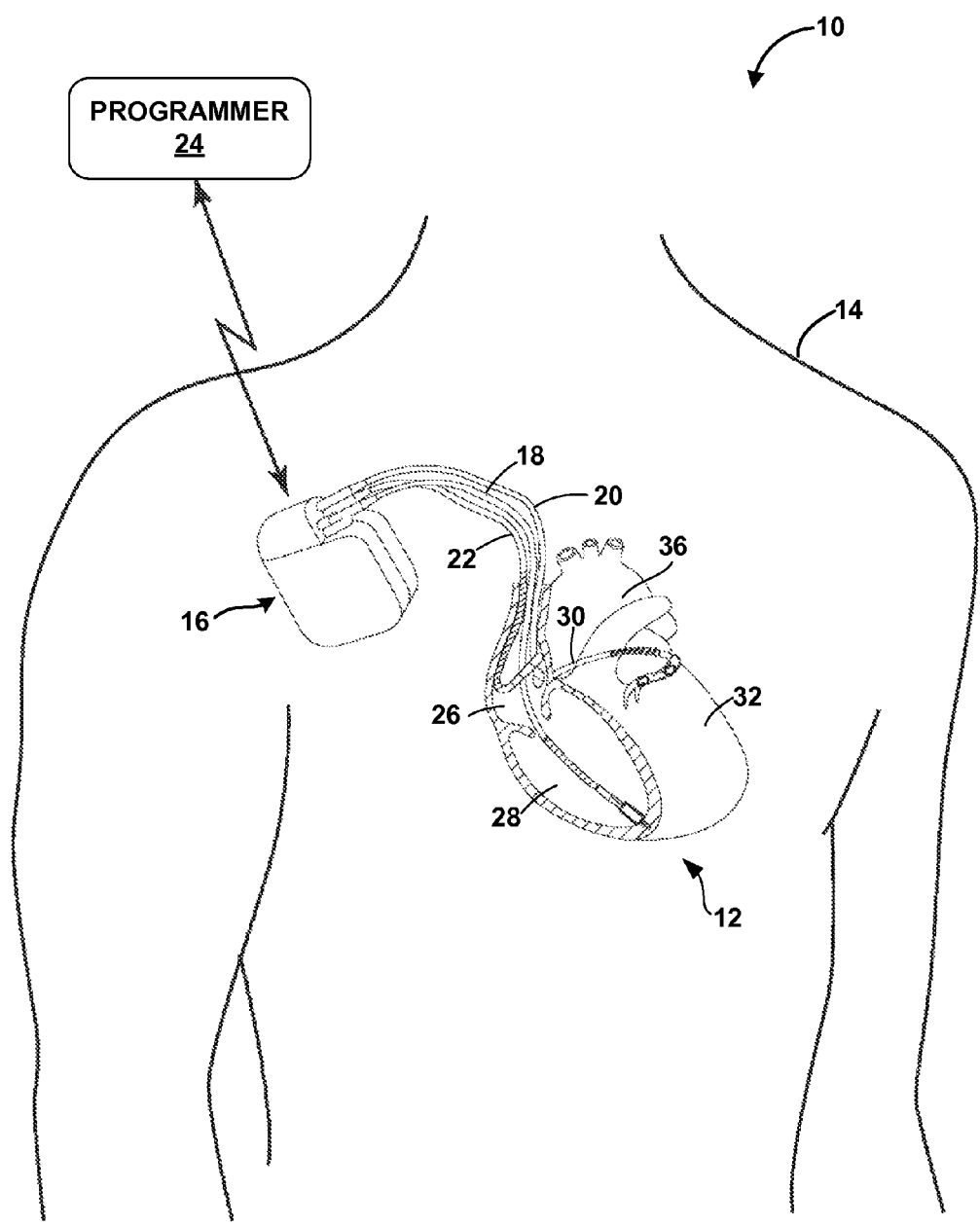
FIG. 1 is a conceptual drawing that illustrates an example system that includes an implantable medical device (IMD) coupled to implantable medical leads.

In general, the disclosure is directed to systems, devices, and techniques that facilitate wireless communication between an IMD and an external wireless telemetry receiver antenna during exposure to a disruptive energy field, such as an energy field generated during an MRI scan, CT scan or another medical procedure, during which full operation (e.g., including wireless telemetry) of the IMD may generally be disfavored. For example, during an MRI scan, wireless telemetry between the IMD and another device may interfere with the MRI scan due to electromagnetic fields generated by the IMD during wireless telemetry. The electromagnetic fields generated by wireless telemetry by the IMD may, in some cases, introduce noise into the MRI image and result in reduced quality of the MRI image. Additionally, magnetic fields generated by the MRI scanner during the MRI scan may interfere with delivery of at least some therapy, such as cardioversion or defibrillation stimulation, by the IMD. For example, the magnetic fields may saturate a transformer core of a transformer used for charging high voltage capacitors for cardioversion or defibrillation stimulation delivered by the IMD.

In some examples, an IMD may be configured in an MRI-compatible operating mode prior to performing an MRI scan on the patient in which the IMD is implanted. The MRI-compatible operating mode may include first and second modes in which a sensing module of the IMD can sense various conditions, such as physiological conditions of the patient or operational conditions of the IMD. However, in the first mode, the MRI-compatible operating mode may generally disable communication via wireless telemetry between the IMD and an external device. In addition, in the first mode, the MRI-compatible operating may at least partially disable therapy delivered by the IMD, such as cardioversion and/or defibrillation therapy. Other therapy such as pacing may be enabled or disabled in the first mode. Hence, therapy may be partially or completely disabled in the first mode. As discussed above, in some examples, wireless telemetry may generate energy fields that may interfere with the MRI scanning process, and/or the MRI scan may interfere with delivery of some therapy, such as cardioversion or defibrillation stimulation.

In accordance with aspects of the disclosure, the MRI-compatible operating mode may include a second mode that allows the IMD to selectively override the disabling of wireless telemetry and to generate and wirelessly transmit a notification of a patient event to an external wireless telemetry receiver antenna. For example, in the second mode, the MRI-compatible operating mode of the IMD may allow the IMD, upon identifying a patient event, to enable wireless telemetry and wirelessly transmit a notification of the patient event to a wireless telemetry receiver antenna. The wireless telemetry receiver antenna may be electrically coupled to any of a variety of external devices that may communicate the notification to a user, such as an MRI technician, radiologist, or other clinician. Alternatively, the wireless telemetry receiver antenna may be coupled to an intermediate external device that may forward the received notification to another external device, which may communicate the notification to a user.

In the first and second modes of the MRI-compatible mode, therapy may be entirely or partially disabled. As discussed above, for example, the IMD may disable delivery of cardioversion and/or defibrillation therapy in the first and second modes of the MRI-compatible mode. Delivery of pacing therapy may be disabled during the first and second modes or, alternatively, the IMD may permit delivery of pacing therapy in the first mode and/or second mode. In some cases, pacing may not be adversely impacted by magnetic fields associated with an MRI scan, and therefore may be delivered during the MRI-compatible mode. Wireless telemetry may be enabled in the second mode so that a notification of a patient event may be communicated from the IMD to a user.

The patient may be located in an electromagnetic interference (EMI) shielded room while undergoing an MRI scan or other medical procedure. For example, MRI scanners may be located in EMI shielded rooms to protect operation of the MRI scanner from interference by external EMI sources. Thus, the IMD may not be able to communicate effectively by wireless telemetry with an external device located outside of the room in which the patient is located. To facilitate wireless communication between the IMD and an external device, the wireless telemetry receiver antenna may be located within the EMI shielded room. In some examples, the wireless telemetry receiver antenna may be electrically coupled to an external device or external intermediate device located within the EMI shielded room. The external device to which the antenna is coupled may, in some examples, be a programmer for the IMD, e.g., a clinician programmer or a programmer with reduced functionality when compared with a clinician programmer. In other examples, the device may include a display device with a user interface and circuitry for converting the notification received from the IMD into a visible, audible, tactile or otherwise perceivable alert to a user, such as a MRI technician, radiologist, or other clinician or caretaker. For example, the device may include a display that is visible by a user through a transparent viewing window between a control room containing the control console for the MRI scanner and the EMI shielded room in which the MRI scanner and the patient are located.

In other examples, the antenna may be electrically coupled via a wired connection to an external device located outside of the EMI shielded room. For example, the antenna may be electrically coupled to the external device through a wall of the EMI shielded room via an electrical cable such as a shielded coaxial electrical cable. The external device may include the control console for the MRI scanner, a programmer for the IMD that is located external to the EMI shielded room, or another device that can convert the received notification to a visible, audible, or otherwise perceivable alert for a user. In some examples, the antenna may be directly electrically coupled to the external device or coupled to an external device via an intermediate device inside the EMI shielded room. The intermediate device may electrically transmit the notification to an external device outside the EMI shield room via a wired electrical connection, as described above, or convert the notification to an optical signal for transmission via an optical waveguide, such as an optical fiber, to the external device outside the EMI shield room. As a further alternative, an intermediate device, such as a programmer or other device, may communicate the notification by transmitting optical signals wirelessly to a device outside the EMI shielded room via a transparent viewing window, e.g., using infrared wireless communication.

The notification may indicate to the user that the patient is experiencing a patient event. A patient event may be detected based on data generated by a sensing module of the IMD. The patient event may be related to a physiological condition, such as a cardiac arrhythmia, asystole, or the like. In particular, the patient event may indicate a ventricular tachycardia or ventricular fibrillation, which may require urgent attention. For example, a patient event may be indicated upon sensing a dangerous ventricular arrhythmia such as ventricular fibrillation. Other examples of patient events may include a seizure or other condition relating to neurological function. Additional examples of patient events may include conditions associated with operation of the IMD, such as an operating mode of the IMD, capture or loss of capture of tissue when delivering electrical stimulation, a magnetic field sensed by a sensor of the IMD, battery status of the IMD, lead or electrical conductor conditions, or sensor operating status. A sensing module of the IMD may be configured to sense a variety of conditions such as physiological conditions or operational conditions, as described above, and generate data indicative of such conditions. The IMD may detect a patient event based on the data generated by the sensing module.

A notification of a patient event may indicate a type of patient event, such as a cardiac arrhythmia, and may optionally include other information, such as an indication of a type of cardiac arrhythmia, or data representing a cardiac electrical signal. The notification of a patient event may allow the user to determine whether intervention is indicated to provide acute medical care for the patient event. In some examples, if the notification indicates a cardiac arrhythmia and the user determines intervention is indicated, the user may contact an interventional cardiology team to administer the appropriate response. Additionally or alternatively, after ceasing the MRI scan, the user may utilize a programmer, if present, to change the operating mode of the IMD from the MRI-compatible operating mode to a standard operating mode in which the IMD may provide electrical stimulation to the patient.

FIG. 1 is a conceptual diagram illustrating an example IMD system 10 that may be used for sensing of physiological parameters of patient 14 and/or to provide therapy to heart 12 of patient 14. System 10 includes IMD 16, which is coupled to leads 18, 20, and 22, and programmer 24. IMD 16 may be, for example, an implantable pacemaker, cardioverter, and/or defibrillator, or a combined pacemaker and cardioverter-defibrillator, that provides electrical signals to heart 12 via electrodes coupled to one or more of leads 18, 20, and 22. Patient 14 is ordinarily, but not necessarily, a human patient.

Although an IMD 16 configured to deliver electrical stimulation to heart 12 is described in the examples herein, the techniques described in this disclosure for enabling sensing and, if indicated, wireless telemetry during an MRI scan may be applicable to other medical devices. In general, the techniques described in this disclosure may be implemented by a medical device, e.g., implantable or external, or any one or more components of a system including such a medical device. As one alternative example, IMD 16 may be a cardiac monitor that monitors a rhythm of heart 12, such as a Medtronic Reveal® XT/DX implantable cardiac monitor, commercially available from Medtronic Inc. of Minneapolis, Minn.

Additionally, while the examples described herein primarily focus on an IMD that senses activity of heart 12 and selectively provides notification to an external device if the IMD detects a cardiac arrhythmia, the techniques described herein may be implemented in other IMDs, and for other patient events. For example, the techniques may be implemented in a neurostimulator that delivers, for example, spinal cord stimulation, deep brain stimulation, peripheral nerve stimulation, pelvic floor stimulation, gastric stimulation, or the like. In examples in which the techniques described herein are implemented in a neurostimulator, such as a deep brain stimulator, the patient event may be, for example, a seizure or other neurological activity.

In the example of FIG. 1, leads 18, 20, 22 extend into the heart 12 of patient 16 to sense physiological signals based on electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not labeled in FIG. 1) coupled to at least one of the leads 18, 20, 22. In some examples, IMD 16 provides pacing stimulation to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., stimulation with increasing energy levels, until a fibrillation of heart 12 is stopped. IMD 16 may detect fibrillation employing one or more fibrillation detection techniques known in the art, and may be configured to identify ventricular arrhythmias such as ventricular tachycardia or ventricular fibrillation.

Although not shown in FIG. 1, in some examples, IMD 16 may employ a sensing module having sensors to sense the electrical signals of heart 12, as described above, in conjunction with leads 18, 20, 22 and associated electrodes, or to sense additional or alternative physiological conditions or parameters, or to sense activity of heart 12 using other types of sensors. For example, in addition or as an alternative to sense amplifiers for electrical cardiac signals, IMD 16 may utilize a sensing module comprising one or more of a pressure sensor, gyroscope, accelerometer, impedance sensor, or the like, to sense physiological parameters including intracardiac or intravascular pressure, posture, respiration, or thoracic impedance. In some examples, the sensing module of IMD 16 also may sense operational conditions of IMD 16, as described above.

In some examples, programmer 24 comprises a computing device, computer workstation, or networked computing device, and may be fixed, portable or handheld. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16. In some examples, at least some of this information may be presented to the user as an alert. For example, in accordance with some examples of the techniques described herein, a detected patient event, such as a cardiac arrhythmia, may cause IMD 16 to transmit a notification or alert to the user via programmer 24.

IMD 16 and programmer 24 may communicate via wireless communication using any techniques known in the art. Examples of communication techniques may include, for example, low frequency inductive telemetry or higher frequency radiofrequency (RF) telemetry, but other techniques are also contemplated. In some examples, for inductive or radio frequency telemetry, programmer 24 may include a programming head that may be placed proximate to the patient's body near the IMD 16 implant site in order to improve the quality or security of communication between IMD 16 and programmer 24. However, a programming head may not be necessary for some forms of telemetry, such as radio frequency telemetry. Inductive telemetry, in one example, may operate in a frequency band centered at approximately 175 kHz. Radio frequency telemetry, in one example, may operate in a frequency band of approximately 402-405 MHz, known as the Medical Implant Communication Services (MICS) band. In some examples, wireless communication between IMD 16 and programmer 24 may initiated by programmer 24 interrogating IMD 16. In other examples, IMD 16 may initiate wireless communication with programmer 24 by, for example, transmitting a notification to programmer 24 upon detecting a patient event, such as a cardiac arrhythmia. IMD 16 may be configured to activate wireless telemetry, without being activated by an external programmer, when an MRI field is detected, e.g., by a magnetic field sensor in the IMD.

Figure 2A:
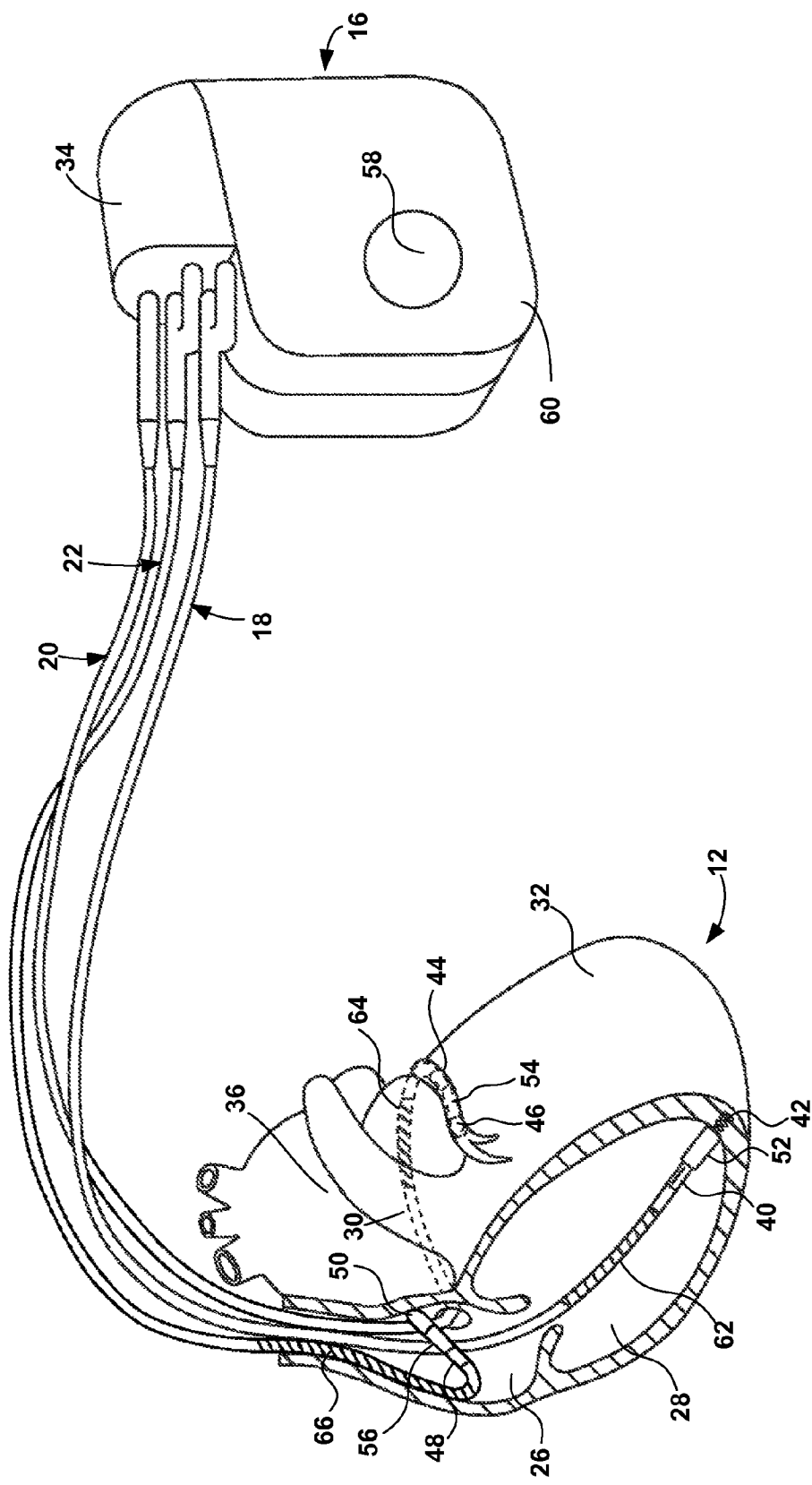
FIG. 2A is a conceptual drawing that illustrates the example IMD and leads of FIG. 1 in conjunction with a heart.

FIG. 2A is a conceptual diagram illustrating IMD 16 and leads 18, 20 and 22 of system 10 in greater detail. Leads 18, 20, 22 may be electrically coupled to a therapy delivery module, e.g., a stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or a lead having another fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing surface of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a therapy delivery module that generates therapeutic stimulation, such as cardiac pacing stimulation and/or defibrillation stimulation, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation shocks to heart 12 via any combination of elongated electrodes 62, 64, 66, and housing electrode 58. Electrodes 58, 62, 64, 66 may also be used to deliver cardioversion shocks to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or patch electrodes instead of or in addition to the transvenous leads 18, 20, 22 illustrated in FIG. 1. Further, as an alternative to IMD 16, such a medical device need not be implanted within patient 14. In examples in which a medical device is not implanted in patient 14, the medical device may deliver defibrillation stimulation and other therapies to heart 12 via percutaneous leads that extend through the skin of patient 14 to a variety of positions within or outside of heart 12 or via external electrodes.

Figure 2B:
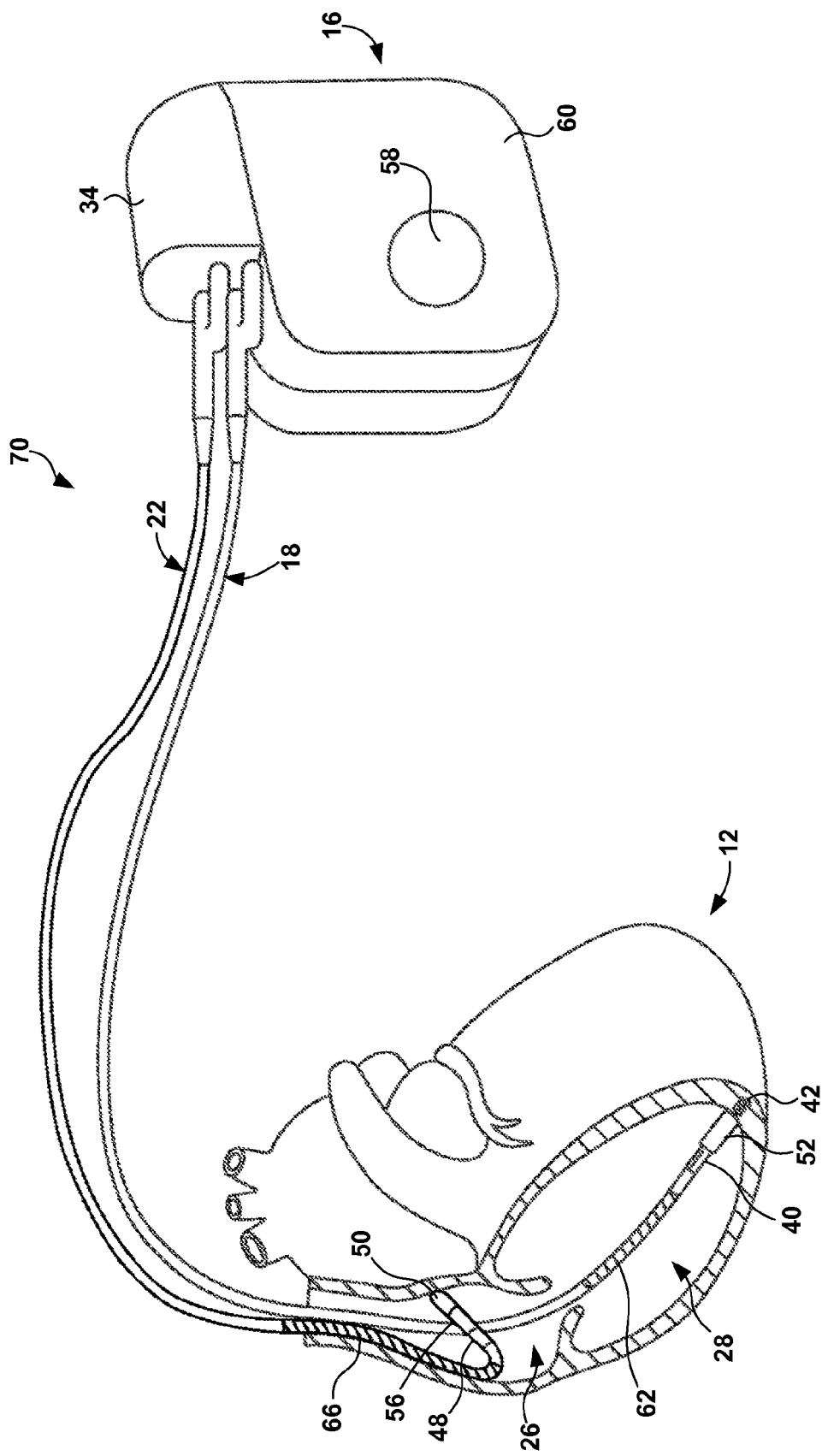
FIG. 2B is a conceptual drawing that illustrates another example IMD coupled to implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2A, and an additional lead located within or proximate to left atrium 36. As another example, other examples of systems may include a single lead that extends from IMD 16 into right atrium 26 or right ventricle 28, or two leads that extend into a respective one of the right ventricle 26 and right atrium 26. An example of this type of system is shown in FIG. 2B. Any electrodes located on these additional leads may be used in sensing and/or stimulation configurations.

FIG. 2B is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, defibrillation or other therapies to heart 12. The techniques described herein may be performed in two lead systems in the manner described herein with respect to three lead systems.

In accordance with aspects of this disclosure, in either of system 10 of FIGS. 1 and 2A or system 70 of FIG. 2B, IMD 16 may be capable of operating in more than one operating mode, at least one of which may be an MRI-compatible operating mode. For example, a user may interact with programmer 24 to select among at least a standard operating mode and an MRI-compatible operating mode for IMD 16. The standard operating mode may enable IMD 16 to perform substantially any function, selected by a clinician programming IMD 16, that IMD 16 is capable of performing. For example, IMD 16 may be capable of sensing electrical activity of heart 12 via electrodes 40, 42, 44, 46, 48, 50, 58, 62, 64, or 66; providing pacing stimulation, defibrillation stimulation, and/or cardioversion stimulation to heart 12 via electrodes 40, 42, 44, 46, 48, 50, 58, 62, 64, 66; communicating with programmer 24 or another device via wireless telemetry; being charged by an external charging device; or the like. In some examples, the standard operating mode may allow the clinician to select a sub-set of functionality for operation of IMD 16. For example, in the standard operating mode, the clinician may configure IMD 16 to enable IMD 16 to sense electrical activity of heart 12 and communicate with programmer 24 via wireless telemetry, but may at least partially disable delivery of electrical stimulation by IMD 16. In other examples, the clinician may configure IMD 16 to enable all functionality that IMD 16 is capable of, e.g., sensing electrical activity of heart 12, providing pacing stimulation, defibrillation stimulation and/or cardioversion stimulation, and communicating wirelessly with programmer 24 via wireless telemetry.

An MRI-compatible operating mode may enable or permit IMD 16 to perform a limited subset of all possible functionalities, which are limited by compatibility of the functionality with an MRI scan. For example, the MRI-compatible operating mode may enable sensing of electrical activity of heart 12 by IMD 16, but may at least partially disable delivery of pacing stimulation (e.g., pacing pulses), defibrillation stimulation and/or cardioversion stimulation (e.g., defibrillation or cardioversion shocks) to heart 12 by IMD 16, and charging of a power source (if rechargeable) of IMD 16. In some examples, the MRI-compatible operating mode may enable IMD 16 to deliver pacing stimulation to heart 12, but may disable delivery of cardioversion and/or defibrillation stimulation. As described above, in some example, an MRI scanner may generate magnetic fields that interfere with charging of high voltage capacitors used to generate defibrillation stimulation signals. For example, the magnetic fields generated by the MRI scanner may saturate a core of a high voltage transformer that transforms the voltage output by the power source of IMD 16 to a voltage used to charge the high voltage capacitors.

In addition, in a first mode of the MRI-compatible operating mode, wireless telemetry may generally be disabled. In accordance with aspects of the disclosure, however, the MRI-compatible operating mode may allow IMD 16 to selectively activate a second mode that enables wireless telemetry and allows IMD 16 to communicate with programmer 24 or another external device via wireless telemetry under predetermined conditions. For example, when configured in the MRI-compatible operating mode, a processor of IMD 16 may generally operate in the first mode and disable wireless telemetry functions, but the processor of IMD 16 may selectively operate in the second mode to enable telemetry when the processor of the IMD 16 identifies a patient event, e.g., based on sensed electrical activity or other sensed activity of heart 12. As an example, a patient event may be indicated when patient 14 is experiencing an arrhythmia of heart 12, such as ventricular fibrillation. In this case, it may be important to identify the patient event and deliver acute medical care to address the patient event.

Described herein are examples of IMD 16 generating and transmitting a notification of a patient event that includes a cardiac arrhythmia or asystole. In some examples, the cardiac arrhythmia may be a tachycardia, such as a ventricular tachycardia, or a fibrillation, such as a ventricular fibrillation. Asystole may be an issue, for example, for pacing-dependent patients generally, but particularly if pacing is disabled during the MRI-compatible mode of IMD 16. As described above, in some examples, the patient event may include a seizure or other physiological condition, or an operational condition of IMD 16. Additionally, the disclosure describes examples in which IMD 16 detects the patient event based on sensed electrical activity of heart 12. In some examples, IMD 16 may generate and transmit a notification of a patient event based on one or more additional or alternative sensed physiological parameters, such as intracardiac or intravascular pressure, posture, respiration, mechanical motion of heart 12, tissue perfusion, or thoracic impedance, or other parameters, in addition to or as an alternative to sensed electrical activity of heart 12. Such additional or alternative parameters may be sensed by any of a variety of suitable sensors, such as accelerometers, pressure sensors, optical sensors, electrodes, or the like. Hence, the sensing module of IMD 16 may include electrical, mechanical or other sensors. In some examples, the patient event may additionally or alternatively include an event associated with an operational condition of IMD 16, such as, for example, capture or loss of capture of tissue when delivering electrical stimulation, level of a magnetic field sensed by a sensor of the IMD, battery status for the IMD, lead or electrical conductor conditions, sensor operating statuses, or the status of the MRI-compatible operating mode.

In the MRI-compatible operating mode, a processor of IMD 16 may detect electrical signals attendant to the depolarization and repolarization of heart 12 ("cardiac electrical signals") via bipolar combinations of electrodes 40, 42, 44, 46, 48, 50, 62, 64 and 66 or unipolar combinations of electrode 58 with one of electrodes 40, 42, 44, 46, 48, 50, 62, 64 and 66. The processor of the IMD 16 receives the electrical signals from the electrodes via the respective leads 18, 20, 22. The processor of IMD 16 may process the cardiac electrical signals according to techniques known in the art to determine whether the cardiac electrical signals indicate a cardiac arrhythmia, such as bradycardia, tachycardia, fibrillation, or the like. In some examples, when the processor of IMD 16 determines that patient 14 is experiencing a cardiac arrhythmia, or other patient event, the processor of IMD 16 enables wireless telemetry. Additionally, the processor of IMD 16 may generate a notification and control telemetry circuitry to transmit the notification to a wireless telemetry receiver antenna (not shown in FIG. 1, 2A or 2B).

In some examples, the processor of IMD 16 may implement additional decisional criteria to determine whether to operate in the second mode and enable wireless telemetry. For example, the processor of IMD 16 may only operate in the second mode and enable wireless telemetry when the processor detects predetermined types of cardiac arrhythmias, such as a ventricular fibrillation or ventricular tachycardia, which may require urgent attention. In such examples, the processor of IMD 16 may not operate in the second mode and enable wireless telemetry when the processor detects other types of cardiac arrhythmias, such as bradycardia or atrial fibrillation, which may not require urgent attention.

In some examples, the processor of IMD 16 may compare the duration of the cardiac arrhythmia to a threshold duration and when the cardiac arrhythmia has continued longer than the threshold duration, the processor may enable wireless telemetry and generate and transmit a notification to the wireless telemetry receiver antenna. When the duration of the cardiac arrhythmia is less than the threshold duration, the processor of IMD 16 may continue to sense electrical activity of heart 12, but may not enable wireless telemetry.

In some examples, the processor of IMD 16 may compare the rate of the cardiac arrhythmia to a threshold rate and when the rate satisfies a predetermined relationship to the threshold rate, the processor may enable wireless telemetry and generate and transmit a notification to the wireless telemetry receiver antenna. For example, when the processor of IMD 16 detects a tachycardia, the processor may determine a heart rate and compare the heart rate to a threshold heart rate. When the determined heart rate is greater than or equal to the threshold heart rate, the processor of IMD 16 may enable wireless telemetry and generate and transmit a notification to the wireless telemetry receiver antenna. When the determined heart rate is less than the threshold heart rate, the processor of IMD 16 may not enable wireless telemetry, but may continue sensing electrical signals of heart 12, determining the heart rate from the cardiac signals, and comparing the determined heart rate to the threshold heart rate.

As another example, when the processor of IMD 16 detects a bradycardia, the processor may determine a heart rate and compare the heart rate to a threshold heart rate. When the determined heart rate is less than or equal to the threshold heart rate, the processor of IMD 16 may enable wireless telemetry and generate and transmit a notification to the wireless telemetry receiver antenna. When the determined heart rate is greater than the threshold heart rate, the processor of IMD 16 may not enable wireless telemetry, but may continue sensing electrical signals of heart 12, determining the heart rate from the cardiac signals, and comparing the determined heart rate to the threshold heart rate. In the case of bradycardia, even if a threshold heart rate is not sensed, sensing of asystole may trigger the second mode.

In some examples, the processor of IMD 16 may implement two or more of the decisional criterion described above, in any combination. For example, the processor of IMD 16 may compare heart rate determined from the electrical activity of heart 12 to a threshold heart rate and may compare a duration of the cardiac arrhythmia to a threshold duration when determining whether to enable wireless telemetry. Other combinations are also possible and within the scope of this disclosure. For example, the processor of IMD 16 may analyze sensed intracardiac pressure and compare the sensed cardiac electrical activity to the sensed intracardial pressure to determine whether to enable wireless telemetry, generate a notification of a patient event, and transmit the notification to a wireless telemetry receiver antenna.

In some examples, the processor of IMD 16 may attempt to deliver stimulation therapy upon detecting the patient event. For example, the processor of IMD 16 may determine, based on one or more of the decisional criteria described above, that patient 14 is experiencing a patient event that includes a ventricular fibrillation. The processor of IMD 16 may then control the therapy delivery module of IMD 16 to generate and deliver defibrillation stimulation to heart 12 via two or more of electrodes 58, 62, 64, 66. In some examples, the therapy delivery module of IMD 16 may not be able to deliver defibrillation stimulation to heart 12, e.g., because the therapy delivery module may not be able to charge the high voltage capacitors used to deliver the defibrillation stimulation due to saturation of the transformer core used to charge the capacitors. As described above, the saturation of the transformer core may be caused by magnetic fields generated by the MRI scanner. In some examples, upon determining that the therapy delivery module of IMD 16 is unable to deliver stimulation therapy to heart 12, the processor of IMD 16 may enter the second mode of the MRI compatible operating mode.

In other examples, upon detecting a patient event, e.g., a ventricular fibrillation, the processor of IMD 16 may determine if the processor is operating in the MRI compatible operating mode or is operating in a standard operating mode. When the processor determines it is operating in the standard operating mode, the processor may deliver appropriate therapy to patient 14. When operating in the MRI compatible operating mode, the IMD may operate in the first mode by default, e.g., a mode in which sensing is enabled but wireless telemetry and at least some therapy are disabled. When the processor determines it is operating in the MRI compatible operating mode, upon detection of a patient event, the processor may enable the second mode of the MRI compatible operating mode.

Once the processor of IMD 16 detects the patient event (based on any of the decisional criteria listed above), the processor may operate in the second mode, and may enable wireless telemetry. In some examples, the processor of IMD 16 may control a telemetry module to generate and transmit the notification of the patient event upon entering the second operating mode. The processor of IMD 16 may, in some examples, automatically transmit the notification to the external device via the wireless telemetry receiver antenna, e.g., without first being interrogated by the external device. In one example, telemetry in IMD 16 may be activated, but not enabled, by placing a telemetry head in proximity to the IMD, either upon detection of the presence of the telemetry head or upon configuration by an external device such as programmer 24. As a further example, telemetry in IMD 16 may be automatically activated when an MRI-compatible mode is selected by a programmer, or when an MRI magnetic field is detected by the IMD while the IMD is an MRI-compatible mode. Automatic activation of telemetry in response to an MRI-compatible mode or detection of a magnetic field may be useful when the notification is to be sent to an external device that is not a programmer 24. In either case, IMD 16 then may enable telemetry to actively transmit a notification when a patient event is detected. In other examples, the processor of IMD 16 may generate the notification, but may not transmit the notification until the processor of IMD 16 is interrogated by the external device, e.g., programmer 24. In some examples, the external device may be configured to periodically interrogate the processor of IMD 16, e.g., at a time when the interrogation may not undesirably interfere with the MRI scan. For example, the external device may interrogate the processor of IMD 16 at times when the MRI scanner is not actively performing a scan of patient 14.

In some examples, the notification that the processor of IMD 16 generates and transmits to the wireless telemetry receiver antenna may be relatively simple and may include an indication that patient 14 is experiencing a patient event, such as a cardiac arrhythmia, and an indication of the type of cardiac arrhythmia that the patient 14 is experiencing, and/or data representing a cardiac electrical signal, such as electrogram (EGM) data. For example, the notification may include a label such as bradycardia, tachycardia, atrial fibrillation, or ventricular fibrillation.

In other examples, the notification that the processor of IMD 16 generates and transmits to the wireless telemetry receiver antenna may include additional or alternative information. For example, the notification may include data representative of the sensed electrical activity of heart 12 based on which the processor determined patient 14 was experiencing a cardiac arrhythmia, a calculated heart rate of patient 14, information regarding an operating mode of IMD 16, other operating parameters of IMD 16, or the like. As a further example, the notification may include marker channel data indicating various cardiac events. In additional examples, the notification may include rating information that indicates a severity of the condition, e.g., on a numeric or other scale. The notification may include any of this information in addition to an indication that patient 14 is experiencing a patient event, or the notification may include any of this information instead of the indication that patient 14 is experiencing a patient event.

Regardless of how the processor of IMD 16 determines when to enable wireless telemetry, when to transmit the notification, or the information included in the notification transmitted to the wireless telemetry receiver antenna, the notification transmitted by the processor of IMD 16 may serve to alert a user of a patient event, such as a cardiac arrhythmia, experienced by patient 14. Upon receiving the notification, the user, who may be an MRI technician, radiologist, cardiologist, or other clinician or caregiver, may suspend the MRI scan and take action or alert qualified personnel, such as a cardiologist or an interventional cardiology team, to take action to administer acute medical care to patient 14. If the patient is experiencing fibrillation, for example, a user may suspend the MRI scan, and apply an external defibrillator to the patient. In some examples, if programmer 24 is available and the user is qualified to operate the programmer, the user may use programmer 24 to change the operating mode of IMD 16 from the MRI-compatible operating mode to a standard operating mode. In some examples, this may allow IMD 16 to deliver electrical stimulation therapy, such as cardioversion or defibrillation stimulation, to patient 14 to address the patient event.

As an illustration, in response to an alert, the user may suspend the MRI scan and move the patient support out of the MRI magnet. The user then may discontinue the MRI-compatible mode and activate IMD 16 to enable delivery of cardioversion and/or defibrillation therapy, e.g., via a patient programmer. Alternatively, IMD 16 may automatically discontinue the MRI-compatible mode and activate IMD 16 6 to enable delivery of cardioversion and/or defibrillation therapy, e.g., upon detection of the patient event and/or the absence of the magnetic field from the MRI scan. As a further alternative, the user may deliver emergency cardioversion and/or defibrillation (e.g., via an external defibrillator) or other appropriate care to patient 14, either within the MRI room or upon transportation of the patient outside the MRI room.

Additionally or alternatively, IMD 16 may be configured to automatically change between the MRI-compatible operating mode and a standard operating mode, e.g., based on a sensor coupled to IMD 16 detecting a magnetic field or detecting an absence of a magnetic field. For example, IMD 16 may include a magnetic field sensor that outputs a signal to a processor of IMD 16 that indicates a sensed external magnetic field intensity, such as a large static magnetic field. In some examples, the processor of IMD 16 may switch from operating in a standard operating mode to the MRI-compatible operating mode when the signal from the magnetic field sensor indicates an external magnetic field intensity that is greater than a threshold magnetic field intensity. Conversely, the processor of IMD 16 may switch from operating in the MRI-compatible operating mode to operating in a standard operating mode when the signal from the magnetic field sensor indicates an external magnetic field intensity that is less than a threshold magnetic field intensity. In some examples, the sensed external magnetic field intensity may need to be greater than or less than the threshold magnetic field intensity for longer than a predetermined amount of time before the processor of IMD 16 will switch operating modes. Further details regarding altering operation of an IMD based on sensed magnetic fields may be found in U.S. Pat. No. 7,050,855 to Zeijlemaker et al., entitled, "MEDICAL IMPLANTABLE SYSTEM FOR REDUCING MAGNETIC RESONANCE EFFECTS," the content of which is incorporated herein by reference in its entirety. Additionally or alternatively, the user may suspend the MRI scan and move patient 14 out of a magnetic field generated by the MRI scanner to cause the processor of IMD 16 to change operating modes, e.g., from the MRI-compatible operating mode to the standard operating mode. Example techniques that may be used by a sensing module of IMD 16 for sensing cardiac signals in the presence of an MRI magnetic field are described in U.S. Patent Publication No. 2007/0238975 to Zeijlemaker, entitled "MEDICAL DEVICE SENSING AND DETECTION DURING MRI," the content of which is incorporated herein by reference in its entirety.

Figure 3:
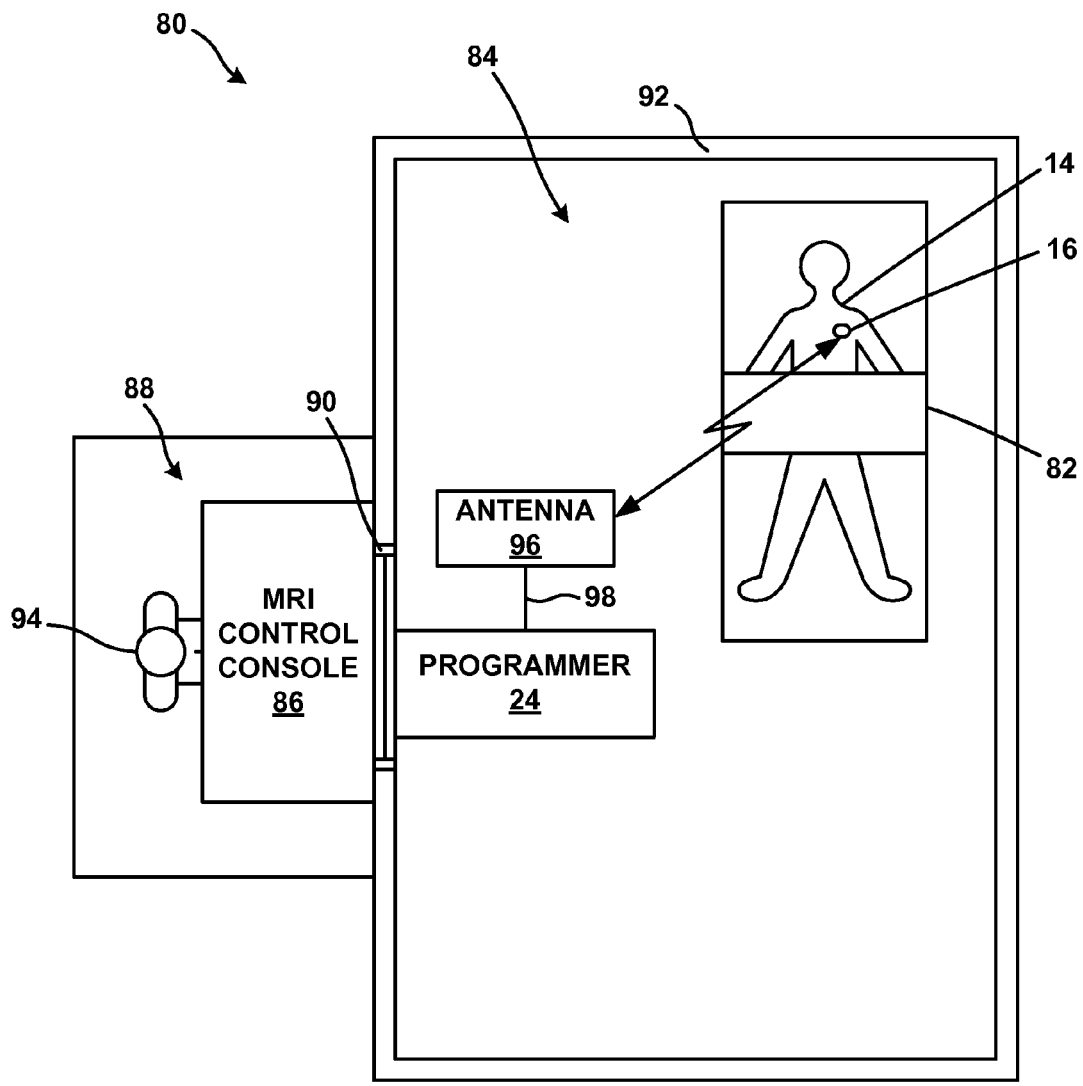
FIG. 3 is a conceptual drawing that illustrates an example system in which an IMD may enable wireless telemetry and transmit a notification to a wireless telemetry receiver antenna during an MRI scan.
Figure 4:
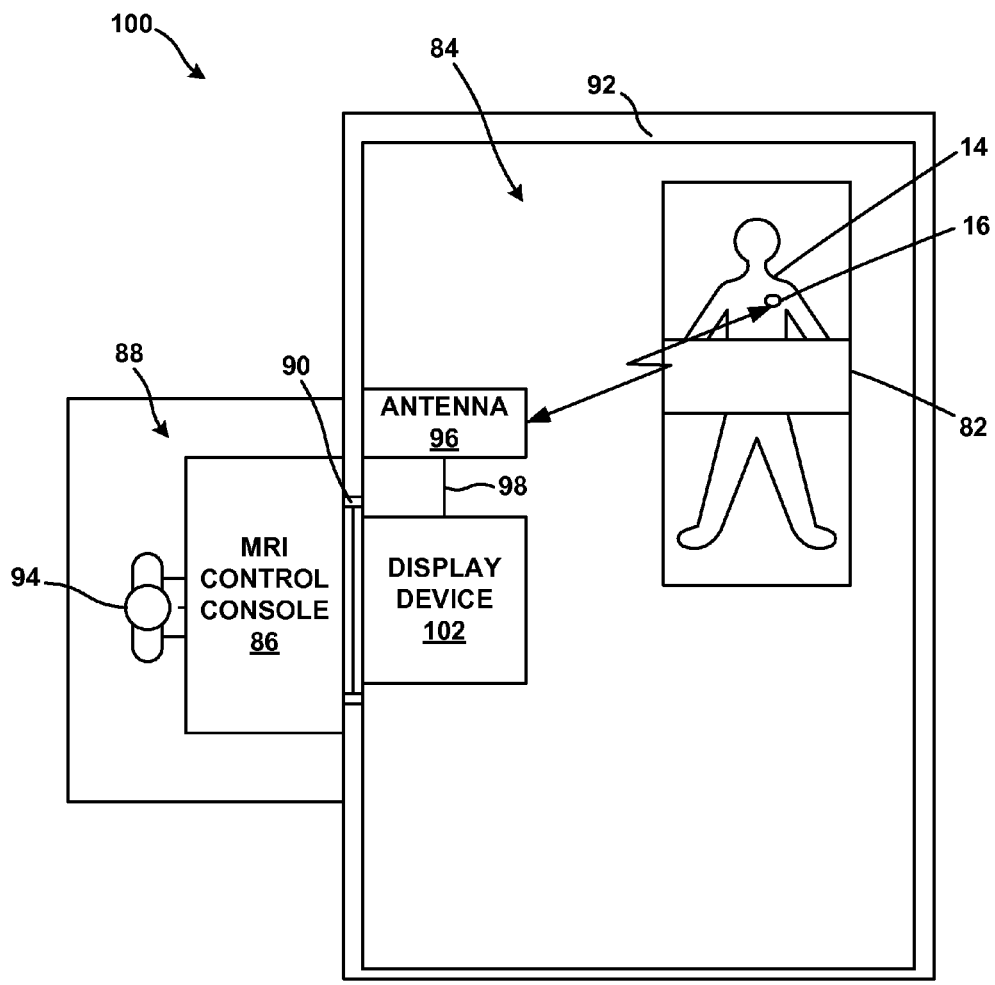
FIG. 4 is a conceptual drawing that illustrates another example system in which an IMD may enable wireless telemetry and transmit a notification to a wireless telemetry receiver antenna during an MRI scan.
Figure 5:
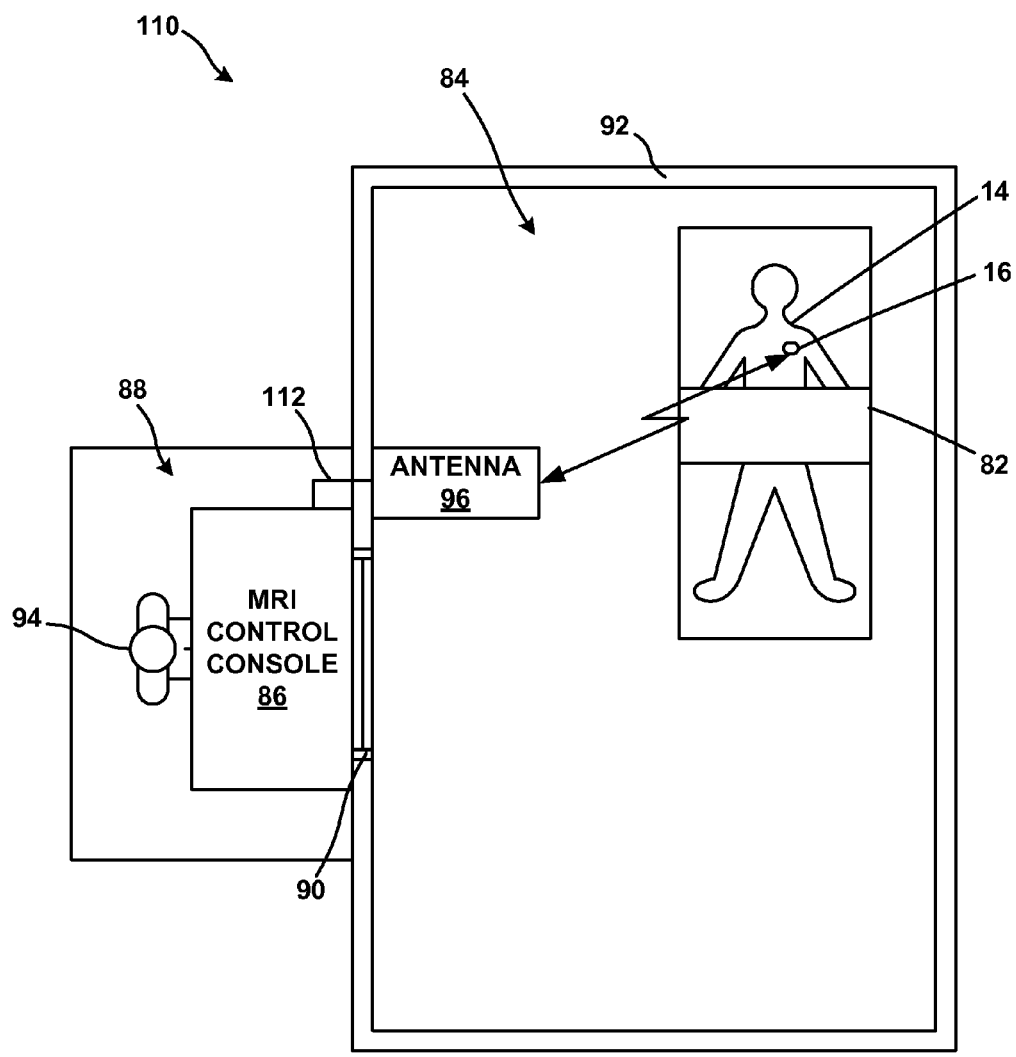
FIG. 5 is a conceptual drawing that illustrates another example system in which an IMD may enable wireless telemetry and transmit a notification to a wireless telemetry receiver antenna during an MRI scan.

FIGS. 3-5 are conceptual diagrams that illustrate example systems in which IMD 16 may be configured to operate in an MRI-compatible operating mode in accordance with the disclosure. FIGS. 3-5 illustrate various examples of external devices to which a wireless telemetry receiver antenna may be coupled. The external devices may receive a notification from IMD 16, and may convert the notification from the form provided by IMD 16 to a visual, audible, or otherwise perceivable alert to a user. As described above, the notification may include at least one of an indication that patient 14 is experiencing a patient event, an indication of the type of patient event, data representative of the sensed cardiac electrical activity, marker channel data indicating cardiac events, rating information that indicates a severity of the patient event, a calculated heart rate, information regarding an operating mode of IMD 16, or other operating parameters of IMD 16.

FIG. 3 illustrates a system 80 that includes an MRI scanner 82 located in an EMI shielded room 84 and an MRI control console 86 located in a separate control room 88. In some examples, between EMI shielded room 84 and control room 88 may be a viewing window 90. Also located in EMI shielded room 84 is a programmer 24, which is coupled to a wireless telemetry receiver antenna 96 ("antenna 96") via a wired electrical connection 98. Programmer 24 may be any external device that is capable of communicating with IMD 16 to retrieve information from IMD 16 and/or to configure operation of IMD 16. For example, as described above with respect to FIG. 1, a user (e.g., user 94) may utilize programmer 24 to retrieve physiological or diagnostic information from IMD 16. The user may also interact with programmer 24 to program IMD 16, e.g., select values for operational parameters of the IMD 16.

In various examples, programmer 24 may reside within EMI shielded room 84, as shown in FIG. 3, and be visible via window 90. In particular, as will be described with reference to FIG. 3, programmer 24 may reside within EMI shield room 84 and be positioned so that information presented on a display of the programmer is visible to a user in control room 88 via viewing window 90. In other examples, programmer 24 may reside outside room 84 and be configured to receive signals from IMD 16 within EMI shielded room 84, e.g., via wired, wireless or other communication media as described in this disclosure, such as an antenna 96 residing within room 84. For example, programmer 24 may reside in control room 88 and be connected to antenna 96 via a wired or wireless connection that extends between rooms 84 and 88.

EMI shielded room 84 may be substantially fully enclosed by EMI shielding 92. EMI shielding 92 may be any apparatus or material that is capable of attenuating electromagnetic fields from one side of EMI shielding 92 on the other side of EMI shielding 92. For example, EMI shielding 92 may attenuate, within EMI shielded room 84, electromagnetic fields that are generated or present outside of EMI shielded room 84. This may reduce electromagnetic fields in EMI shielded room 84 other than the electromagnetic fields generated within room 84, e.g., electromagnetic fields generated by operation of MRI scanner 82 and/or IMD 16. In this way, EMI shielding 92 may improve quality of images collected by MRI scanner 82 by reducing noise in the images due to external EMI.

EMI shielding 92 functions in both directions, i.e., EMI shielding 92 also attenuates, outside of room 84, electromagnetic fields generated within EMI shielded room 84. This may reduce the amplitude outside of EMI shielded room 84 of electromagnetic fields generated by MRI scanner 82, but may also impede or substantially prevent wireless telemetry between IMD 16 and a device, such as a programmer, located outside of EMI shielded room 84. In some examples, EMI shielding may be a Faraday cage, Faraday shield, or another suitable EMI attenuating device or material.

MRI control console 86 is located in control room 88 to control operation of MRI scanner 82. MRI control console 86 may present a user interface to a user 94 that facilitates control of the MRI scanner 82. In some examples, MRI control console 86 may allow user 94, who may be an MRI technician or a clinician, to configure MRI scanner 82 to operate in a manner with which IMD 16 is compatible. For example, the user may configure MRI scanner 82 to produce a magnetic field having a magnitude compatible with IMD 16. MRI scanner 82 may comprise a conventional MRI scanner, and may include, for example, a single channel or multiple channel RF coil. In some examples, viewing window 90 may be located between control room 88 and EMI shielded room 84 to allow user 94 to observe patient 14 and MRI scanner 82 during the MRI procedure.

As described above, during the MRI scan, IMD 16 may be configured in an MRI-compatible operating mode. In some examples, the MRI-compatible operating mode may include a first mode and a second mode. In the first mode of the MRI-compatible operating mode, IMD 16 may be able to sense physiological parameters of patient 14, such as electrical signals of heart 12, but communication between IMD 16 and an external device via wireless telemetry may be disabled. In some examples, as described above, the MRI-compatible operating mode may also at least partially disable delivery of electrical stimulation by IMD 16 in first and second modes. In the MRI-compatible operating mode, IMD 16 may disable charging of capacitors associated with higher voltage cardioversion and defibrillation therapy delivery of IMD 16.

In accordance with aspects of this disclosure, a processor of IMD 16 may selectively enter the second mode and override the disabling of wireless telemetry upon detecting certain, predetermined cardiac events. For example, the processor of IMD 16 may enter the second mode and override the disabling of wireless telemetry upon sensing a patient event, such as a cardiac arrhythmia. In some examples, the processor of IMD 16 may implement additional, optional decision criteria, such as, for example, determining the type of cardiac arrhythmia, comparing a determined heart rate of patient 14 to a threshold heart rate, attempting to deliver electrical stimulation therapy to patient 14, or comparing a duration of the detected cardiac arrhythmia to a threshold duration. In some examples, the processor of IMD 16 may enable wireless telemetry when one or more of the decisional criteria are satisfied. Further details regarding the operation of IMD 16 and enabling of wireless telemetry by the processor of IMD 16 may be found elsewhere herein.

When the processor of IMD 16 enables wireless telemetry, the processor may cause a telemetry module of the IMD to generate and transmit a notification of the detected cardiac arrhythmia to antenna 96. In some examples, the processor of IMD 16 may automatically transmit the notification to programmer 24 via antenna 96, e.g., without first being interrogated by programmer 24. Automatic transmission may be especially desirable if the patient event relates to a condition that requires immediate attention, such as ventricular fibrillation. In other examples, the processor of IMD 16 may generate the notification, but may not transmit the notification until the processor of IMD 16 is interrogated by programmer 24. In some examples, programmer 24 may be configured to periodically interrogate the processor of IMD 16, e.g., at a time when the interrogation may not undesirably interfere with the MRI scan. For example, programmer 24 may interrogate the processor of IMD 16 at times when MRI scanner 82 is not actively performing a scan of patient 14.

As shown in FIG. 3, antenna 96 is located within EMI shielded room 84, and may be electrically coupled to an external device in the form of programmer 24 via a wired connection 98. In other examples, as illustrated in FIGS. 4 and 5, antenna 96 may be electrically coupled to different external devices. Because antenna 96 is within EMI shielded room 84, it can more reliably receive telemetry signals from IMD 16 than an antenna located outside of EMI shielded room 84.

In some examples, antenna 96 may be enclosed within a programming head. The programming head may be configured to be placed proximate to IMD 16, e.g., near an external surface of patient 14, to facilitate wireless communication between IMD 16 and programmer 24. In other examples, antenna 96 may be an internal antenna within a housing of programmer 24, or may be an external antenna, located outside of a housing of programmer 24 and not within a programming head of programmer 24. In general, antenna 96 may be located at any location within EMI shielded room 84 that allows wireless communication between IMD 16 and programmer 24 via antenna 96.

IMD 16 may communicate with programmer 24 via low frequency or radio frequency telemetry, or via other telemetry techniques, such as proximal inductive coupling. Regardless of the technique by which IMD 16 wirelessly communicates with programmer 24, the processor of IMD 16 may control a telemetry module to generate and transmit a notification of the cardiac arrhythmia or other patient event to programmer 24 via antenna 96. As described above, in some examples, the notification may include a simple indication that patient 14 is experiencing a cardiac arrhythmia. Alternatively or additionally, the notification may include the type of arrhythmia that patient 14 is experiencing, a determined heart rate of patient 14, a representative cardiac electrical signal for patient 14, marker channel data indicating various cardiac events, rating information that indicates a severity of the cardiac arrhythmia, e.g., on a numeric or other scale, or the like.

In some examples, the content of the notification may be based on the functionality of the receiving device. For example, when the device receiving the notification is programmer 24, the notification may include more detail, such as a representative cardiac electrical signal in addition to the indication that patient 14 is experiencing a cardiac arrhythmia, while when the device receiving the notification is a display device 102 (FIG. 4), the notification may include less detail, such as only the indication that patient 14 is experiencing a cardiac arrhythmia or only the type of arrhythmia that patient 14 is experiencing. In other examples, a notification that is received by programmer 24 may include less detail, and a notification that is received by display device 102 may include more detail. Hence, in some examples, various amounts of detail may be included in the notification according to the capability of the receiving device, e.g., programmer 24 or display device 102.

As shown in FIG. 3, in some examples, programmer 24 may be located within EMI shielded room 84 at a location so that programmer 24 is visible to user 94 through viewing window 90. More particularly, programmer 24 may include a user interface, such as a display screen, one or more indicator lights, an acoustic transducer, a vibrator or other mechanism for producing tactile feedback, or the like, by which an alert may be output by a processor of programmer 24. To facilitate viewing, in some examples, programmer 24 may be mounted on or near viewing window 90, e.g., via any of a variety of mounting hardware, stands, or platforms, or using adhesives or other fastening devices. When the processor of programmer 24 receives, from the processor of IMD 16 via antenna 96, the notification that patient 14 is experiencing a cardiac arrhythmia, the processor of programmer 24 may process the notification to convert it to an alert that can be output by programmer 24 via a user interface. The alert may include, for example, a continuously lighted or flashing indicator light, a textual or graphical message or symbol on a display, an audible tone, such as a buzz or beep, a tactile alert such as vibrating or pulsing, or the like. In some examples in which programmer 24 is located in EMI shielded room 84 and is visible to user 94 through window 90, a visible alert, such as a message on a display or a flashing or continuously lighted indicator light, may be more effective than an audible or tactile alert.

In some examples, the notification may additionally or alternatively include cardiac electrical signal (e.g., an electrocardiogram or ECG) data. In some implementations, the processor of programmer 24 may process the received cardiac electrical signal data and display a representation of the cardiac electrical signal on a display of programmer 24. Additionally or alternatively, the processor of programmer 24 may display a determined heart rate of patient 14 (determined by the processor of IMD 16 or the processor of programmer 24), or other information related to operation of IMD 16, such as the operating mode, the electrode configuration IMD 16 is using for sensing cardiac electrical signals, or the like. Hence, programmer 24 or display device 102 (FIG. 4) may display intra-cardiac signals and rhythm, as well as programmed modes and states of IMD 16.

In some implementations, when the processor of programmer 24 outputs the alert via the user interface, the processor may continue outputting the alert until a user, e.g., user 94, interacts with the user interface of programmer 24 to clear or dismiss the alert. This may operate as a confirmation that user 94 has perceived and addressed the alert, e.g., by stopping the MRI scan, observing and/or communicating with patient 14, and if required, contacting a cardiologist or an interventional cardiology team.

In some examples, in addition to presenting the alert to the user 94, programmer 24 may allow user 94 or another qualified user to communicate with IMD 16. For example, user 94 may interact with programmer 24 to retrieve physiological or diagnostic information from IMD 16. User 94 may also interact with programmer 24 to program IMD 16, e.g., to select or change values for operational parameters of IMD 16 or operating modes of IMD 16.

For example, user 94 may use programmer 24 to retrieve information from IMD 16 regarding the rhythm of heart 12, trends therein over time, or arrhythmic episodes. As another example, user 94 may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the operational performance or integrity of IMD 16 or other components of system 10, such as leads 18, 20 and 22, or a power source of IMD 16.

As other examples, user 94 may use programmer 24 to change operating modes of IMD 16, e.g., from the standard operating mode to an MRI-compatible operating mode or vice versa. In some examples, after perceiving the alert from programmer 24 and ceasing the MRI scan, user 94 may utilize programmer 24 to change the operating mode of IMD 16 from the MRI-compatible operating mode to a standard operating mode, in which IMD 16 may deliver electrical stimulation therapy, e.g., pacing, defibrillation, and/or cardioversion, to the heart of patient 14.

As described above, programmer 24 may be configured to generate a visible notification or alert that is visible by a user in control room 88 via window 90. Alternatively, or additionally, programmer 24 may be configured to transmit information to another device outside of EMI shielded room 84 via wired or wireless communication. For example, programmer 24 may transmit information to MRI control console 86 or another device in control room 88 via an electrical cable or optical waveguide that penetrates a wall of room 84. Alternatively, programmer 24 may generate wireless optical signals for transmission to MRI control console 86 via viewing window 90. For example, programmer 24 may include an infrared optical transmitter to transmit infrared optical signals to an infrared receiver associated with MRI control console 86 via viewing window 90, e.g., using a wireless IrDA (Infrared Data Association) communication link. MRI control console 86 then may generate a notification, alert or other information indicative of a patient event, based on the communication received from programmer 24. Hence, MRI control console 86 may include a telemetry interface. In addition, MRI control console 86 may receive cardiac signal information and may include digital and/or analog circuitry for processing of intra-cardiac signal data and generation of visible or audible alerts in the event of a patient event.

FIG. 4 is a conceptual diagram of another system 100 in which IMD 16 may enable wireless telemetry during an MRI scan to transmit a notification of a cardiac arrhythmia or other patient event to an external device. Similar to system 80 of FIG. 3, system 100 includes MRI scanner 82 located within EMI shielded room 84 and MRI control console 86 located in a separate control room 88. Window 90 provides a viewing port between control room 88 and EMI shielded room 84. EMI shielded room may be substantially enclosed by EMI shielding 92, which attenuates electromagnetic energy on either side of EMI shielding 92. User 94 controls MRI scanner 82 using MRI control console 86, and may be situated within control room 88 with a view of MRI scanner 82 and patient 14 during the MRI scan.

In the example illustrated in FIG. 4, wireless telemetry receiver antenna 96 is electrically coupled to display device 102 via wired electrical connection 98. Wired electrical connection 98 may be any suitable electrical conductor. As described above with respect to FIG. 3, antenna 96 may in some examples be located proximate to patient 14 and/or IMD 16. In other examples, antenna 96 may be located within EMI shielded room 84 in any location that allows antenna 96 to receive wireless telemetry signals from IMD 16. In some examples, antenna 96 may be located within a housing of display device 102 (e.g., may be an internal antenna). In other examples, antenna 96 may be an external antenna coupled to display device 102 via wired electrical connection 98.

In some examples, display device 102 may provide less functionality than programmer 24 of FIG. 4. For example, display device 102 may not generally allow user 94 or another qualified user to communicate with IMD 16 to retrieve information from IMD 16 or program IMD 16. Instead, display device 102 may be a simple device that allows receipt of notifications from IMD 16 via wireless telemetry and display of the information received in the notification to user 94.

For example, display device 102 may include a wireless telemetry module that is configured to a receive notification from IMD 16 via wireless telemetry, a processor that is configured to process the received notification and output an alert based on information in the received notification, and a user interface for outputting the alert and receiving inputs from user 94.

Similar to programmer 24, display device 102 may be located within EMI shielded room 84 at a location that is visible from control room 88 through window 90. In some examples, display device 102 may be sufficiently small that device 102 may be removably coupled or attached to window 90. In other examples, display device 102 may not be coupled or attached to window 90 and may instead be located to be visible to user 94 through window 90. Like programmer 24, display device 102 may be positioned on or near window 90 via any of a variety of mounting hardware, stands, or platforms, or using adhesives or other fastening devices.

In some examples, display device 102 may include a user interface, such as a display screen, one or more indicator lights, an acoustic transducer, or the like, via which an alert may be output by the processor of display device 102. When the processor of display device 102 receives from the processor of IMD 16 via antenna 96 the notification that patient 14 is experiencing a cardiac arrhythmia, the processor of display device 102 may process the notification to convert it to an alert that can be output by the processor of display device 102 via the user interface. The alert may include, for example, a continuously lighted or flashing indicator light, a textual or graphical message or symbol on a display, an audible tone, such as a buzz or beep, or the like. In some examples in which display device 102 is located in EMI shielded room 84 and is visible to user 94 through window 90, a visible alert, such as a message on a display or a flashing or continuously lighted indicator light, may be more effective than an audible alert.

In some examples, the processor of IMD 16 may generate and transmit the notification of the patient event to display device 102 automatically upon entering the second operating mode, e.g., without first being interrogated by display device 102. As described above, in some examples, the notification may additionally or alternatively include other information, such as cardiac electrical signal data (e.g., an electrocardiogram or ECG), a heart rate of patient 14, marker channel data indicating various cardiac events, rating information that indicates a severity of the condition, e.g., on a numeric or other scale, or information related to operation of IMD 16. In some examples, the processor of display device 102 may process the information and display the information via the user interface of display device 102. Regardless of the content of the notification, in some implementations, when the processor of display device 102 outputs the alert via the user interface, the processor may continue outputting the alert until a user, e.g., user 94, interacts with the user interface of display device 102 to clear or dismiss the alert.

FIG. 5 is a conceptual diagram of another system 110 in which IMD 16 may enable wireless telemetry during an MRI scan to transmit a notification of a cardiac arrhythmia to an external device. Similar to FIGS. 3 and 4, system 110 of FIG. 5 includes MRI scanner 82 located within EMI shielded room 84 and MRI control console 86 located in a separate control room 88. Window 90 provides a viewing port between control room 88 and EMI shielded room 84. EMI shielded room 84 may be substantially enclosed by EMI shielding 92, which attenuates electromagnetic energy on either side of EMI shielding 92. User 94 controls MRI scanner 82 using MRI control console 86, and may be situated within control room 88 with a view of MRI scanner 82 and patient 14 during the MRI scan.

In the example illustrated in FIG. 5, wireless telemetry receiver antenna 96 is communicatively coupled to MRI control console 86 via wired connection 112. MRI control console 86 is located within control room 88 while antenna 96 is located within MRI shielded room 84. In this way, wired connection 112 allows communication between antenna 96 in EMI shielded room 84 and MRI control console 86 in control room 88. Because wired connection 112 extends from control room 88 to EMI shielded room 84, wired connection 112 may penetrate EMI shielding 92 and provide a path by which electromagnetic energy may enter or exit EMI shielded room 84. In some examples, to reduce EMI effects, wired connection 112 may comprise a shielded coaxial cable. Antenna 96 may be coupled directly to wired connection 112 or coupled indirectly via an intermediate device, such as a device that amplifies, converts and/or processes the signal received by antenna 96 for transmission via the wired connection.

In some examples, instead of an electrical connection, wired connection 112 may comprise an optical conductor such as an optical fiber or other optical waveguide. In this case, wireless telemetry receiver antenna 96 may include conversion circuitry for converting the received signal to an optical signal, such as an infrared (IR) signal, for transmission via wired connection 112. In other examples, instead of wireless telemetry receiver antenna 96 being connected to MRI control console 86 via wired connection 112, wireless telemetry receiver antenna 96 may be communicatively coupled to MRI control console 86 through viewing window 90 via an infrared communication link, e.g., an IrDA (Infrared Data Association) communication link, such as that described with reference to programmer 24 in FIG. 3. In such examples, wireless telemetry receiver antenna 96 may include circuitry for converting the received signal to an infrared or other optical signal, and MRI control console 86 may include corresponding circuitry for converting the received infrared signal to a signal format that a processor of MRI control console 86 can process. In this example, the optical signal may be wirelessly transmitted through the air, rather than through an optical waveguide, and received by console 86 via viewing window 90. In some examples, redundant communication may be provided, such as wired communication of electrical signals, wireless communication of optical signals, and/or wired communication of optical signals via an optical waveguide.

As described above with respect to FIG. 3, antenna 96 may in some examples be located proximate to patient 14 and/or IMD 16. In other examples, antenna 96 may be located within EMI shielded room 84 in any location that allows antenna 96 to receive wireless telemetry signals from IMD 16.

In some examples, MRI control console 86 may include a user interface, such as a screen, one or more indicator lights, an acoustic transducer, or the like, by which an alert may be output by the processor of MRI control console 86. When the processor of MRI control console 86 receives from the processor of IMD 16 via antenna 96 the notification that patient 14 is experiencing a cardiac arrhythmia, the processor of MRI control console 86 may process the notification to convert it to an alert that can be output by the processor of MRI control console 86 via the user interface. The alert may include, for example, a continuously lighted or flashing indicator light, a message on a display, an audible tone, such as a buzz or beep, or the like. In some examples in which MRI control console 86 is located in EMI shielded room 84 and is visible to user 94 through window 90, a visible alert, such as a message on a display or a flashing or continuously lighted indicator light, may be more effective than an audible alert.

As described above, in some examples, the notification may optionally include additional information, such as cardiac electrical signal data (e.g., an electrocardiogram or ECG), a heart rate of patient 14, or information related to operation of IMD 16. A processor of programmer 24, display device 102, or console 86 may process the additional information and display the information to a user.

Although antenna 96 is shown in FIG. 5 as being communicatively coupled to MRI control console 86 via wired connection 98, in other examples, antenna 96 may be communicatively coupled via wired connection 98 to another device located within control room 88. For example, programmer 24 or display device 102 may be located within control room 88 and antenna 96 may be communicatively coupled to programmer 24 or display device 102 via wired connection 98.

Figure 6:
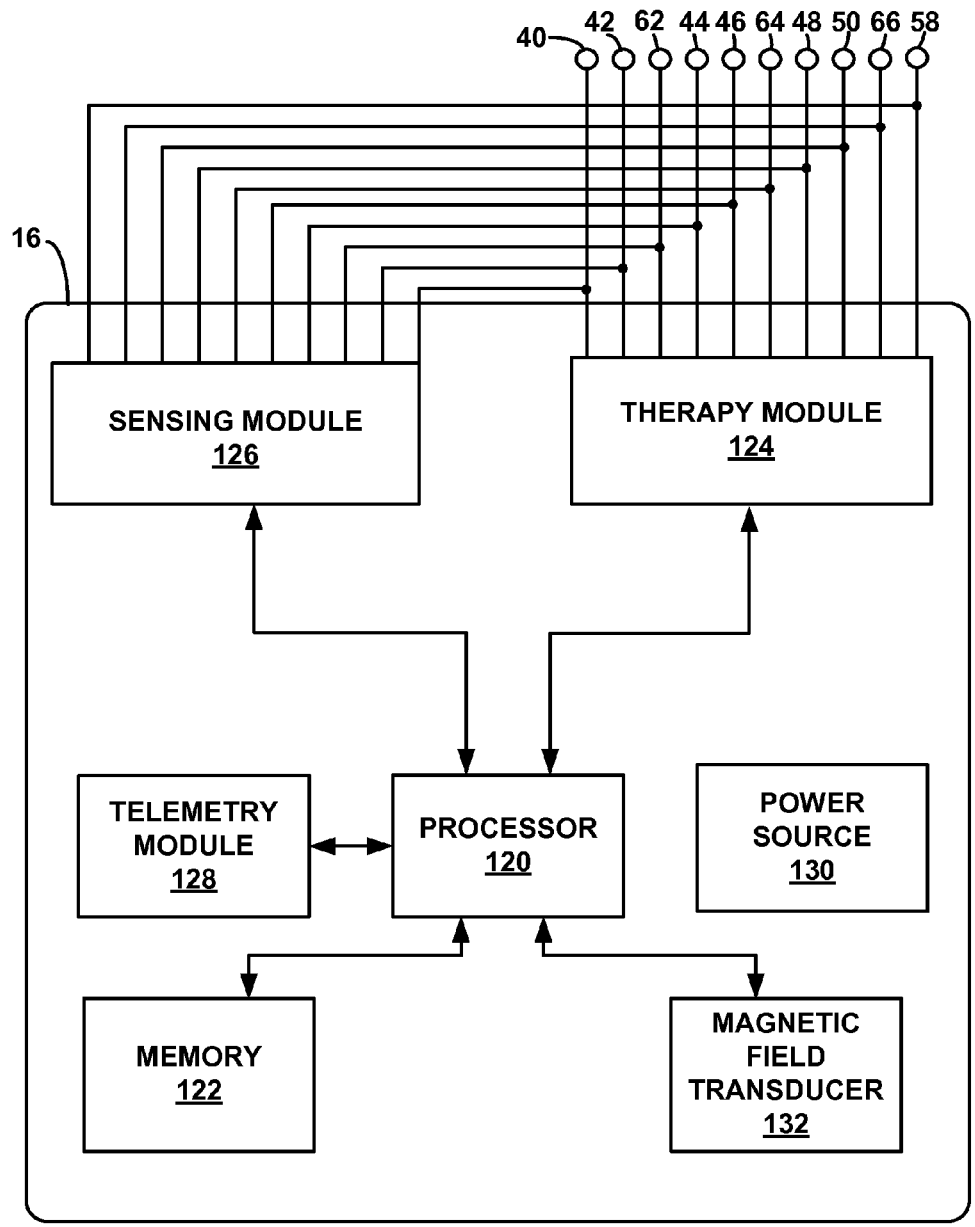
FIG. 6 is a functional block diagram that illustrates an example configuration of the IMD of FIGS. 1-5.

FIG. 6 is a functional block diagram illustrating an example configuration of IMD 16 in accordance with aspects of the disclosure. In the illustrated example, IMD 16 includes a processor 120, memory 122, therapy delivery module 124, sensing module 126, telemetry module 128, and power source 130. As described above, processor 120 may be configured to operate in more than one operating mode, at least one of which may be an MRI-compatible operating mode. For example, a user may interact with programmer 24 to select among at least a standard operating mode and an MRI-compatible operating mode for processor 120. The standard operating mode may enable processor 120 to perform substantially any function selected by a clinician programming IMD 16 that processor 120 is capable of performing.

For example, processor 120 may be capable of sensing electrical activity of heart 12 via sensing module 126 and electrodes 40, 42, 44, 46, 48, 50, 58, 62, 64, or 66; providing pacing stimulation, defibrillation stimulation, and/or cardioversion stimulation to heart 12 via therapy delivery module 124 and electrodes 40, 42, 44, 46, 48, 50, 58, 62, 64, 66; communicating wirelessly with programmer 24 or another device via telemetry module 128; allowing charging of power source 130 (if rechargeable) by an external charging device; or the like. In some examples, the standard operating mode may allow the clinician to select a sub-set of all possible functionality for operation of processor 120. For example, in the standard operating mode, the clinician may configure IMD 16 to enable processor 120 to sense electrical activity of heart 12 via sensing module 126 and communicate with programmer 24 via telemetry module 128, and enable therapy delivery module 124 to deliver pacing, cardioversion and defibrillation therapy, as needed. Although sensing of electrical activity of heart 12 is described for purposes of illustration, sensing module 126 may be configured to sense other physiological conditions.

In contrast, the MRI-compatible operating mode may enable or permit processor 120 to perform a limited subset of all possible functionalities, which may be limited by compatibility of the functionality with an MRI scan. In some examples, as described above, the MRI-compatible operating mode may include a first mode and a second mode. In the first mode, the MRI-compatible operating mode may enable sensing of electrical activity of heart 12 via sensing module 126, but may disable wireless telemetry via telemetry module 128. In some examples, in the first mode of the MRI-compatible operating mode, IMD 16 may disable delivery of all electrical stimulation, such as pacing, cardioversion and defibrillation, to heart 12 by therapy delivery module 124. Alternatively, in the first mode of the MRI-compatible operating mode, IMD 16 may at least partially disable therapy by disabling cardioversion and defibrillation, which may be impacted by the MRI scan, but permitting pacing, which may be generally compatible with the MRI scan. In some examples, the IMD 16 also may disable charging of power source 130 (if rechargeable) by an external charging device.

In accordance with aspects of the disclosure, in the MRI-compatible operating mode additionally, processor 120 may enable communication with programmer 24 or another external device via wireless communication by telemetry module 128 under predetermined conditions. For example, the MRI-compatible operating mode may, in the first mode, disable telemetry module 128, such that telemetry is disabled and therapy is at least partially disabled, but may allow processor 120 to enter a second mode, in which processor 120 enables telemetry module 128, when the processor 120 determines, based on sensed electrical activity of heart 12 or other sensed conditions, that patient 14 is experiencing a patient event, such as an arrhythmia of heart 12.

Memory 122 includes computer-readable instructions that, when executed by processor 120, cause IMD 16 and processor 120 to perform various functions attributed to IMD 16 and processor 80 herein. Memory 122 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 120 may include any one or more of a microprocessor, a controller, a digital signal processor (DSP), an application specific integrated circuit (ASIC), a field-programmable gate array (FPGA), or equivalent discrete or analog logic circuitry. In some examples, processor 120 may include multiple components, such as any combination of one or more microprocessors, one or more controllers, one or more DSPs, one or more ASICs, and/or one or more FPGAs, as well as other discrete or integrated logic circuitry. The functions attributed to processor 120 herein may be embodied as software, firmware, hardware or any combination thereof.

Processor 120 controls therapy delivery module 124 to deliver stimulation therapy to heart 12 according to a selected one or more of therapy programs, which may be stored in memory 122. For example, processor 120 may control therapy delivery module 124 to deliver electrical pulses with the amplitudes, pulse widths, frequency, or electrode polarities specified by the selected one or more therapy programs.

Therapy delivery module 124 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, therapy delivery module 124 is configured to generate and deliver electrical stimulation therapy to heart 12. For example, therapy delivery module 124 may deliver electrical stimulation to heart 12 via at least two electrodes 58, 62, 64, 66. In some examples, therapy delivery module 124 delivers pacing pulses, and cardioversion and/or defibrillation stimulation in the form of electrical shocks. In some examples, therapy delivery module 124 may include separate circuits for delivery of cardiac pacing and cardioversion/defibrillation.

Therapy delivery module 124 may include a switch module and processor 120 may use the switch module to select, e.g., via a data/address bus, which of the available electrodes are used to deliver cardioversion or defibrillation shocks or pacing pulses. The switch module may include a switch array, switch matrix, multiplexer, or any other type of switching device suitable to selectively couple stimulation energy to selected electrodes.

Electrical sensing module 126 monitors signals from at least one of electrodes 40, 42, 44, 46, 48, 50, 58, 62, 64 or 66 in order to monitor electrical activity of heart 12. Sensing module 126 may also include a switch module to select which of the available electrodes 40, 42, 44, 46, 48, 50, 58, 62, 64 or 66 are used to sense the cardiac electrical activity, depending upon which electrode combination is used in the current sensing configuration. In some examples, processor 120 may select the electrodes that function as sense electrodes, i.e., select the sensing configuration, via the switch module within sensing module 126.

Sensing module 126 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 120, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 120 may control the functionality of sensing module 126 by providing signals via a data/address bus.

Processor 120 may include a timing and control module, which may be embodied as hardware, firmware, software, or any combination thereof. The timing and control module may comprise a dedicated hardware circuit, such as an ASIC, separate from other processor 120 components, such as a microprocessor, or a software module executed by a component of processor 120, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 126 for a time interval during and after delivery of electrical stimulation to heart 12. The durations of these intervals may be determined by processor 120 in response to stored data in memory 122. The timing and control module of processor 120 may also determine the amplitude of the cardiac pacing pulses.

Interval counters implemented by the timing and control module of processor 120 may be reset upon sensing of R-waves and P-waves with detection channels of sensing module 126. In examples in which IMD 16 provides pacing, therapy delivery module 124 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 120 may reset the interval counters upon the generation of pacing pulses by therapy delivery module 124, and thereby control the basic timing of cardiac pacing functions, including anti-tachyarrhythmia pacing.

The value of the count present in the interval counters when reset by sensed R-waves and P-waves may be used by processor 120 to measure the durations of R-R intervals, P-P intervals, P-R intervals and R-P intervals, which are measurements that may be stored in memory 122. Processor 120 may use the count in the interval counters to detect a tachyarrhythmia event, such as atrial or ventricular fibrillation or an atrial or ventricular tachycardia. A portion of memory 122 may be configured as a plurality of recirculating buffers, capable of holding series of measured intervals, which may be analyzed by processor 120 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 120 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 120 in other examples.

In some examples, processor 120 may determine that tachyarrhythmia or fibrillation has occurred by identification of shortened R-R (or P-P) interval lengths. Generally, processor 120 detects tachycardia when the interval length falls below 220 milliseconds (ms) and fibrillation when the interval length falls below 180 ms. These interval lengths are merely examples, and a user may define the interval lengths as desired, which may then be stored within memory 122. This interval length may need to be detected for a certain number of consecutive cycles, for a certain percentage of cycles within a running window, or a running average for a certain number of cardiac cycles, as examples.

An MRI scan may interfere with sensing of cardiac electrical signals by sensing module 126. In some implementations, processor 120 or sensing module 126 may implement an MRI sensing algorithm that facilitates sensing of cardiac electrical signals during an MRI scan. For example, IMD 16 may include an optional magnetic field transducer 132. In some examples, magnetic field transducer 132 may detect an MRI gradient magnetic field via inductive coupling of the field with one of three orthogonal coils, depending upon the orientation of the gradient magnetic field. In other examples, magnetic field transducer 132 may be a linear magnetic field detector that is capable of detecting magnetic field gradients, and which also is capable of detecting magnetic field intensities. Magnetic field transducer 132 may provide an output indicating the intensity of the magnetic field to processor 120, which may be a relatively unprocessed signal, or may be a indication of a relative intensity of the magnetic field, e.g., no magnetic field, low intensity magnetic field, or high intensity magnetic field. The output of magnetic field transducer 132 may be provided to processor 120, which may implement the MRI sensing algorithm upon detection of a gradient magnetic field.

In some examples, the MRI sensing algorithm includes introduction of blanking periods for masking a sensing artifact attributable to gradient magnetic fields caused by the MRI scan. The blanking period may be sufficiently long to result in sensing module 126 not detecting signals induced in leads 18, 20, 22 by the gradient magnetic field and subsequent RF bursts generated by the MRI scanner 82 (FIGS. 3-5). For example, the blanking period may be between about 10 milliseconds and about 150 milliseconds.

In other examples, the MRI sensing algorithm includes storing cardiac signal events in memory 122 to provide a cardiac event history. Upon sensing a gradient magnetic field via magnetic field transducer 132, processor 120 may extrapolate predicted cardiac signal events during the gradient magnetic field and subsequent RF bursts. When sensing module 126 senses electrical activity, processor 120 may determine whether to categorize the electrical activity as a cardiac event or a virtual event.

If the electrical activity does not coincide with a gradient field event, processor 120 categorizes the electrical activity as a cardiac event. If the electrical activity coincides with a predicted cardiac signal event but does not coincide with a gradient field event, processor 120 categorizes the electrical activity as a cardiac event. However, if the electrical activity coincides with both a gradient field event and a predicted cardiac signal event, the electrical activity is categorized as a virtual event. Processor 120 may store a count of the cardiac events and the virtual events in memory 122. When the count of the consecutive virtual events passes a threshold value, processor 120 may ignore electrical sensing for a predetermined time period.

Additionally or optionally, the MRI sensing algorithm may include modified signal conditioning by sensing module 126, such as attenuation of RF frequency signals (e.g., between about 6 MHZ and about 300 MHz). Further details regarding an MRI sensing algorithm may be found in the aforementioned U.S. Patent Application Publication No. 2007/0238975 to Zeijlemaker, entitled, "MEDICAL DEVICE SENSING AND DETECTION DURING MRI," the content of which is incorporated herein by reference in its entirety.

When processor 120 is configured to operate in a standard operating mode, in the event that processor 120 detects an atrial or ventricular tachyarrhythmia based on signals from sensing module 126, and an anti-tachyarrhythmia pacing regimen is desired, timing intervals for controlling the generation of anti-tachyarrhythmia pacing therapies by therapy delivery module 124 may be loaded by processor 120 into the timing and control module to control the operation of the escape interval counters therein and to define refractory periods during which detection of R-waves and P-waves is ineffective to restart the escape interval counters for the an anti-tachyarrhythmia pacing. In the event that processor 120 detects an atrial or ventricular tachyarrhythmia based on signals from sensing module 126, and a cardioversion or defibrillation stimulation is desired, processor 120 may control the amplitude, form and timing of the stimulation delivered by therapy delivery module 124.

When processor 120 is configured to operate in a MRI-compatible operating mode, in the event that processor 120 detects a patient event, such as cardiac arrhythmia, processor 120 enters the second mode and may enable telemetry module 128. In some examples, processor 120 may generate and transmit a notification of the patient event via telemetry module 128 to programmer 24 or another external device. Additionally, in some examples, processor 120 may control therapy delivery module 124 to attempt to deliver stimulation therapy, such as defibrillation stimulation, to heart 12 upon detecting a patient event, such as a ventricular arrhythmia.

Telemetry module 128 includes any suitable hardware, firmware, software or any combination thereof for communicating with another device, such as programmer 24, display device 102, and/or MRI control console 86 (e.g., via wireless telemetry receiver antenna 96). Under the control of processor 120, telemetry module 128 may receive downlink telemetry from and send uplink telemetry to programmer 24 with the aid of an antenna, which may be internal and/or external. Processor 120 may provide the data to be uplinked to programmer 24 and the control signals for the telemetry circuit within telemetry module 128, e.g., via an address/data bus. In some examples, telemetry module 128 may provide received data to processor 120 via a multiplexer.

In some examples, processor 120 may transmit, with a notification of a patient event, atrial and ventricular heart signals, e.g., EGMs, produced by atrial and ventricular sense amplifier circuits within sensing module 126 to programmer 24. Programmer 24 may interrogate IMD 16 to receive the heart signals. Processor 120 may store heart signals within memory 122, and retrieve stored heart signals from memory 122. Processor 120 may also generate and store event marker codes indicative of different cardiac events that sensing module 126 detects, and transmit the marker codes to programmer 24 with a notification. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the notification through a network such as the Medtronic CareLink® Network developed by Medtronic, Inc., of Minneapolis, Minn., or some other network linking patient 14 to a clinician.

In accordance with aspects of the disclosure, processor 120 may be configured in an MRI-compatible operating mode and may sense cardiac electrical signals of patient 14 and monitor the cardiac electrical signals to determine whether patient 14 is experiencing a cardiac arrhythmia. In some examples, processor 120 may determine that tachyarrhythmia has occurred by identification of shortened R-R (or P-P) interval lengths. Generally, processor 120 detects tachycardia when the interval length falls below 220 milliseconds (ms) and fibrillation when the interval length falls below 180 ms. These interval lengths are merely examples, and a user may define the interval lengths as desired, which may then be stored within memory 122. Conversely, processor 120 may determine that bradyarrhythmia has occurred by identification of lengthened R-R (or P-P) interval lengths. In some examples, prior to determining that a cardiac electrical signal indicates a cardiac arrhythmia, sensing module 126 may need to detect the interval length indicative of the particular cardiac arrhythmia for a certain number of consecutive cycles, for a certain percentage of cycles within a running window, or a running average for a certain number of cardiac cycles, as examples.

In some examples, when processor 120 determines that a tachyarrhythmia, fibrillation, or bradyarrhythmia has occurred, processor 120 enters the second mode and enables telemetry module 128. In some example, processor 120 generates a notification of the patient event, such as tachyarrhythmia, fibrillation, or bradyarrhythmia, and transmits the notification via telemetry module 128 and antenna 96 to an external device, such as programmer 24, display device 102, or MRI control console 86. As described above, in some examples, the notification that the processor 120 generates and transmits may be relatively simple and may include an indication that patient 14 is experiencing a cardiac arrhythmia and an indication of the type of cardiac arrhythmia that the patient 14 is experiencing. For example, the notification may include a label such as bradycardia, atrial or ventricular tachycardia, or atrial or ventricular fibrillation.

In other examples, the notification that processor 120 generates and transmits may include additional or alternative information. For example, the notification may include data representative of the sensed cardiac electrical activity based on which processor 120 determined patient 14 was experiencing a cardiac arrhythmia, a calculated heart rate of patient 14, information regarding an operating mode of IMD 16, other operating parameters of IMD 16, or the like.

In some examples, prior to enabling telemetry module 128, processor 120 may implement additional decisional criteria. For example, processor 120 may only enable telemetry module 128 when processor 120 detects a predetermined type of cardiac arrhythmia, such as ventricular fibrillation or ventricular tachycardia. In such examples, processor 120 may not enable telemetry module 120 when processor 120 detects other types of cardiac arrhythmias, such as a bradycardia or an atrial tachycardia or fibrillation.

In some examples, processor 120 may compare the duration of the cardiac arrhythmia (e.g., a count of to a number of consecutive R-R or P-P intervals) to threshold duration (e.g., a threshold count) and when the cardiac arrhythmia has continued longer than the threshold duration, processor 120 may enable telemetry module 128 and generate and transmit a notification to the wireless telemetry receiver antenna 96. When the duration of the cardiac arrhythmia is less than the threshold duration, processor 120 may continue to sense electrical activity of heart 12 via sensing module 126, but may not enable telemetry module 128.

In some examples, processor 120 may compare the rate of the cardiac arrhythmia to a threshold rate (e.g., the R-R or P-P interval duration to a threshold interval duration) and when the rate satisfies a predetermined relationship to the threshold rate, processor 120 may enable telemetry module 128. For example, when processor 120 detects a tachycardia, processor 120 compare the R-R or P-P interval to a threshold R-R or P-P interval. When the interval is less than or equal to the threshold interval, processor 120 may enable telemetry module 128. When the determined interval is greater than the threshold interval, processor 120 may not enable telemetry module 128, but may continue sensing cardiac electrical signals via sensing module 126. In some examples, the threshold interval may be equal to the interval at which processor 120 categorizes the cardiac electrical signal as indicating a tachycardia (e.g., 220 ms). In other examples, the threshold interval may be equal to a different value (e.g., between 220 ms and 180 ms).

Processor 120 may implement two or more of the decisional criterion described above, in any combination. For example, processor 120 may compare the interval determined from the cardiac electrical activity to a threshold interval and may compare a duration of the cardiac arrhythmia to a threshold duration when determining whether to enable telemetry module 128. Other combinations are also possible and within the scope of this disclosure.

Additionally or alternatively, processor 120 may control therapy delivery module 124 to attempt to deliver stimulation therapy upon detecting the patient event. For example, processor 120 may determine, based on one or more of the decisional criteria described above, that patient 14 is experiencing a patient event that includes a ventricular fibrillation. Processor 120 may then control therapy delivery module 124 to generate and deliver defibrillation stimulation to heart 12 via two or more of electrodes 58, 62, 64, 66. In some examples, therapy delivery module 124 may not be able to deliver defibrillation stimulation to heart 12, e.g., because therapy delivery module 124 may not be able to charge the high voltage capacitors used to deliver the defibrillation stimulation due to saturation of the transformer core used to charge the capacitors. As described above, the saturation of the transformer core may be caused by magnetic fields generated by the MRI scanner. In some examples, upon determining that therapy delivery module 124 is unable to deliver stimulation therapy to heart 12, processor 120 may enter the second mode of the MRI-compatible operating mode.

In other examples, upon detecting a patient event, e.g., a ventricular fibrillation, processor 120 may determine if processor 120 is operating in the MRI compatible operating mode or is operating in a standard operating mode. When processor 120 determines it is operating in the standard operating mode, processor 120 may control therapy delivery module 124 to deliver appropriate therapy to patient 14. When processor 120 determines it is operating in the MRI compatible operating mode, processor 120 may enable the second mode of the MRI compatible operating mode.

Once processor 120 detects the patient event (based on any of the decisional criteria listed above), processor 120 may operate IMD 16 in the second mode, and may enable telemetry module 128. In some examples, processor 120 may generate and transmit the notification of the patient event upon entering the second operating mode. Processor 120 may, in some examples, automatically transmit the notification to the external device via the telemetry module 128 and wireless telemetry receiver antenna 96 (FIGS. 3-5), e.g., without first being interrogated by the external device. In other examples, processor 120 may generate the notification, but may not transmit the notification until processor 120 is interrogated by the external device, e.g., programmer 24. In some examples, the external device may be configured to periodically interrogate processor 120, e.g., at a time when the interrogation may not undesirably interfere with the MRI scan. For example, the external device may interrogate processor 120 at times when the MRI scanner is not actively performing a scan of patient 14.

The various components of IMD 16 are coupled to power source 130, which may include a rechargeable or non-rechargeable battery. A non-rechargeable battery may be selected to last for several years, while a rechargeable battery may be inductively charged from an external device, e.g., on a daily or weekly basis.

Figure 7:
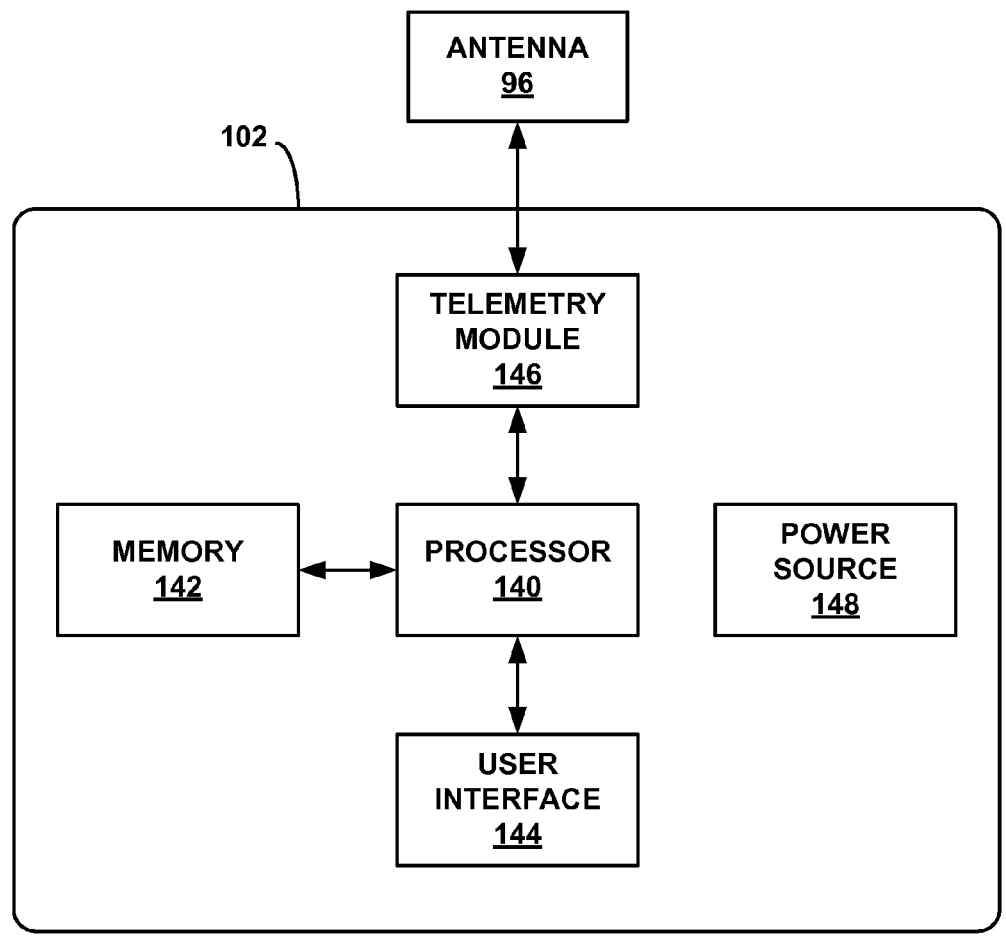
FIG. 7 is a functional block diagram that illustrates an example configuration of a device coupled to a wireless telemetry receiver antenna to receive information from an IMD.

FIG. 7 is functional block diagram illustrating an example configuration of display device 102. As shown in FIG. 7, display device 102 may include a processor 140, memory 142, user interface 144, telemetry module 146, and power source 148. Display device 102 may be a dedicated hardware device with dedicated software for receiving notifications from IMD 16 via wireless telemetry, as illustrated in FIG. 4. Alternatively, display device 102 may be an off-the-shelf computing device running an application that enables display device 102 to receive notifications from IMD 16 via wireless telemetry.

Processor 140 can take the form one or more microprocessors, DSPs, ASICs, FPGAs, programmable logic circuitry, or the like, and the functions attributed to processor 140 herein may be embodied as hardware, firmware, software or any combination thereof. Memory 142 may store instructions that cause processor 140 to provide the functionality ascribed to display device 102 herein, and information used by processor 140 to provide the functionality ascribed to display device 102 herein. Memory 142 may include any fixed or removable magnetic, optical, or electrical media, such as RAM, ROM, CD-ROM, hard or floppy magnetic disks, EEPROM, or the like.

Display device 102 may communicate wirelessly with IMD 16 via antenna 96, such as by using RF communication or proximal inductive interaction. This wireless communication is supported by telemetry module 146, which may be coupled to wireless telemetry receiver antenna 96. Antenna 96 may be an internal antenna within a housing of display device 102 or an external antenna. In some example, antenna 96 may be an external antenna that may be placed proximate to IMD 16, as described above with reference to FIG. 1. Telemetry module 146 may be similar to telemetry module 128 of IMD 16 (FIG. 6).

As described above, processor 120 of IMD 16 may control a telemetry module to generate and transmit a notification to display device 102 upon determining that patient 14 is experiencing a cardiac arrhythmia. In particular, processor 120 of IMD 16 transmits the notification via telemetry module 128 of IMD 16, antenna 96 coupled to display device 102, and telemetry module 146 of display device 102. In some examples, the notification may include a simple indication that patient 14 is experiencing a cardiac arrhythmia or other patient event. Alternatively or additionally, the notification may include the type of arrhythmia that patient 14 is experiencing, a determined heart rate of patient 14, a representative cardiac electrical signal for patient 14, or the like. In some examples, processor 140 interrogates processor 120 of IMD 16 periodically to retrieve any notification generated by processor 120. In other examples, processor 120 of IMD 16 may transmit the notification to processor 140 via antenna 96 and telemetry modules 128, 146 automatically upon generating the notification, without being interrogated by processor 140.

Display device 102 includes a user interface 144, which may include input devices that a user (e.g., user 94) utilizes to interact with display device 102 and output devices by which processor 140 outputs information for user 94 to perceive. In some examples, the input devices of user interface 144 may include one or more buttons, toggle switches, keys (e.g., a keypad or keyboard), a mouse, a touchscreen, or the like. The output devices of user interface 144 may include at least one of a display, indicator lights, an acoustic transducer, or the like.

Processor 140 may receive the notification from IMD 16 via telemetry module 146 and may process the notification to convert the data in the notification from the form in which it was transmitted to a form appropriate for output via user interface 144. For example, processor 140 may convert the data in the notification to pixels for output on an external display, words or other sounds for output via an acoustic transducer, or a continuous or flashing illumination of one or more indicator lights.

In some examples, the notification may additionally or alternatively include a cardiac electrical signal (e.g., an electrocardiogram or ECG). In some implementations, processor 140 may process the received cardiac electrical signal and display a representation of the cardiac electrical signal on a display of display device 102. Additionally or alternatively, processor 140 may display a determined heart rate of patient 14 (determined by the processor 120 of IMD 16 or the processor 140), or other information related to operation of IMD 16, such as the operating mode, the electrode configuration IMD 16 is using for sensing cardiac electrical signals, or the like.

In some implementations, when processor 140 outputs the alert via user interface 144, processor 140 may continue outputting the alert until a user, e.g., user 94, interacts with user interface 144 to clear or dismiss the alert. This may operate as a confirmation that user 94 has perceived and addressed the alert, e.g., by stopping the MRI scan, observing and/or communicating with patient 14, and if required, contacting a cardiologist or an interventional cardiology team.

Power source 148 delivers operating power to the components of display device 102. Power source 148 may include a battery and a power generation circuit to produce the operating power. In some examples, the battery may be rechargeable to allow extended operation.

Figure 8:
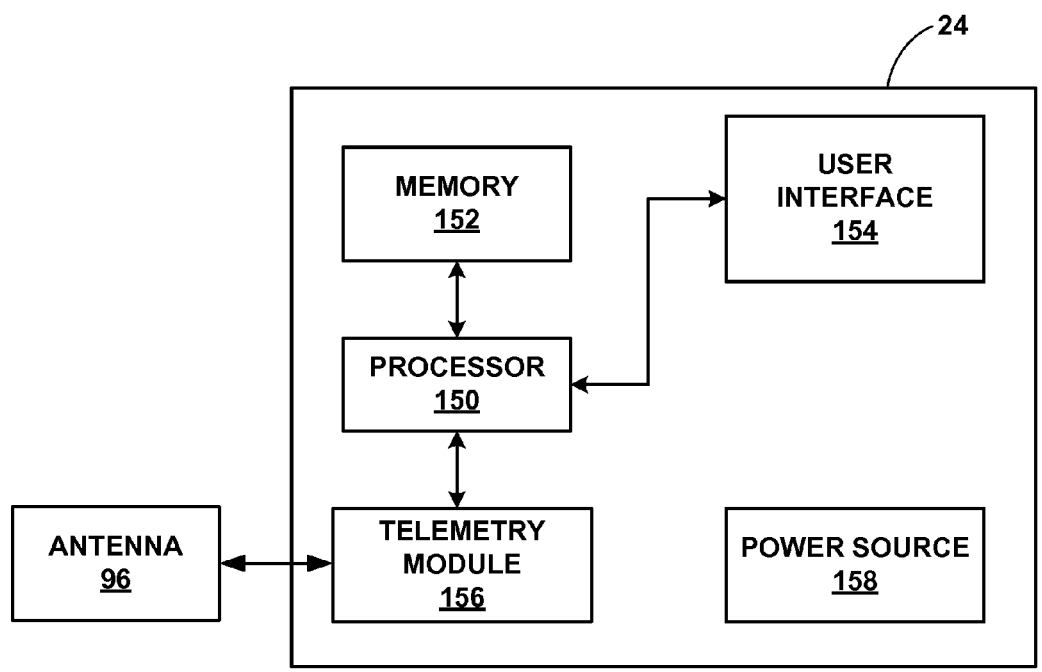
FIG. 8 is a functional block diagram that illustrates an example configuration of the programmer of FIGS. 1 and 3.

FIG. 8 is functional block diagram illustrating an example configuration of programmer 24. As shown in FIG. 8, programmer 24 may include a processor 150, memory 152, user interface 154, telemetry module 156, and power source 158. Programmer 24 may be a dedicated hardware device with dedicated software for programming of IMD 16. Alternatively, programmer 24 may be an off-the-shelf computing device running an application that enables programmer 24 to program IMD 16.

A user (e.g., user 94) may use programmer 24 to select therapy programs (e.g., sets of stimulation parameters), generate new therapy programs, modify therapy programs through individual or global adjustments or transmit the new programs to a medical device, such as IMD 16 (FIG. 1). Additionally, user 94 may interact with programmer 24 to change an operating mode of IMD 16, e.g., from a standard operating mode to an MRI-compatible operating mode or vice versa. User 94 may interact with programmer 24 via user interface 154, which may include display to present graphical user interface to a user, and a keypad or another mechanism for receiving input from a user. In addition, the user 94 may receive an alert from IMD 16 indicating a potential cardiac arrhythmia via programmer 24.

Processor 150 can take the form one or more microprocessors, DSPs, ASICs, FPGAs, programmable logic circuitry, or the like, and the functions attributed to processor 150 herein may be embodied as hardware, firmware, software or any combination thereof. Memory 152 may store instructions that cause processor 150 to provide the functionality ascribed to programmer 24 herein, and information used by processor 150 to provide the functionality ascribed to programmer 24 herein. Memory 152 may include any fixed or removable magnetic, optical, or electrical media, such as RAM, ROM, CD-ROM, hard or floppy magnetic disks, EEPROM, or the like. Memory 152 may also include a removable memory portion that may be used to provide memory updates or increases in memory capacities. A removable memory may also allow patient data to be easily transferred to another computing device, or to be removed before programmer 24 is used to program therapy for another patient.

Processor 150 may communicate wirelessly with processor 120 of IMD 16, such as using RF communication or proximal inductive interaction. This wireless communication is possible through the use of telemetry module 156, which may be coupled to wireless telemetry receiver antenna 96. Antenna 96 may be an internal antenna or an external antenna. An external antenna that is coupled to programmer 24 may correspond to the programming head that may be placed over an IMD 16 near heart 12, as described above with reference to FIG. 1. In other examples, antenna 96 may not be located within a programming head. Telemetry module 156 may be similar to telemetry module 128 of IMD 16 (FIG. 6).

As described above, processor 120 of IMD 16 may control a telemetry module to generate and transmit a notification to display device 102 upon determining that patient 14 is experiencing a cardiac arrhythmia or other patient event. In particular, processor 120 of IMD 16 transmits the notification via telemetry module 128 of IMD 16, antenna 96 coupled to display device programmer 24, and telemetry module 156 of programmer 24. In some examples, the notification may include a simple indication that patient 14 is experiencing a cardiac arrhythmia. Alternatively or additionally, the notification may include the type of arrhythmia that patient 14 is experiencing, a determined heart rate of patient 14, a representative cardiac electrical signal for patient 14, or the like. In some examples, processor 150 interrogates processor 120 of IMD 16 periodically to retrieve any notification generated by processor 120. In other examples, processor 120 of IMD 16 may transmit the notification to processor 150 via antenna 96 and telemetry modules 128, 156 automatically upon generating the notification, without being interrogated by processor 150.

Programmer 24 includes a user interface 154, which may include input devices that a user (e.g., user 94) utilizes to interact with programmer 24 and output devices via which processor 150 outputs information for user 94 to perceive. In some examples, the input devices of user interface 154 may include one or more buttons, toggle switches, keys (e.g., a keypad or keyboard), a mouse, a touchscreen, or the like. The output devices of user interface 154 may include at least one of a display, indicator lights, an acoustic transducer, or the like.

Processor 150 may receive the notification from IMD 16 via telemetry module 146 and may process the notification to convert the data in the notification from the form in which it was transmitted to a form appropriate for output via user interface 154. For example, processor 150 may convert the data in the notification to pixels for output on an external display, words or other sounds for output via an acoustic transducer, or a continuous or flashing illumination of one or more indicator lights.

In some examples, the notification may optionally include a cardiac electrical signal (e.g., an electrocardiogram or ECG). In some implementations, processor 150 may process the received cardiac electrical signal and display a representation of the cardiac electrical signal on a display of programmer 24. Additionally or alternatively, processor 150 may display a determined heart rate of patient 14 (determined by the processor 120 of IMD 16 or the processor 150), or other information related to operation of IMD 16, such as the operating mode, the electrode configuration IMD 16 is using for sensing cardiac electrical signals, or the like.

In some implementations, when processor 150 outputs the alert via user interface 154, processor 150 may continue outputting the alert until a user, e.g., user 94, interacts with user interface 154 to clear or dismiss the alert. This may operate as a confirmation that user 94 has perceived and addressed the alert, e.g., by stopping the MRI scan, observing and/or communicating with patient 14, and if required, contacting a cardiologist or an interventional cardiology team.

In some examples, user 94 may use programmer 24 to change operating modes of IMD 16, e.g., from the standard operating mode to an MRI-compatible operating mode or vice versa. In some examples, after perceiving the alert from programmer 24, user 94 may utilize programmer 24 to change the operating mode of IMD 16 from the MRI-compatible operating mode to a standard operating mode, in which IMD 16 may deliver electrical stimulation, e.g., pacing, defibrillation, and/or cardioversion, to the heart of patient 14.

Telemetry module 156 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. For example, using IrDA, programmer 24 may communicate with external console 86 via window 90. An additional computing device in communication with programmer 24 may be a networked device such as a server capable of processing information retrieved from IMD 16.

Power source 158 delivers operating power to the components of programmer 24. Power source 158 may include a battery and a power generation circuit to produce the operating power. In some examples, the battery may be rechargeable to allow extended operation.

Figure 9:
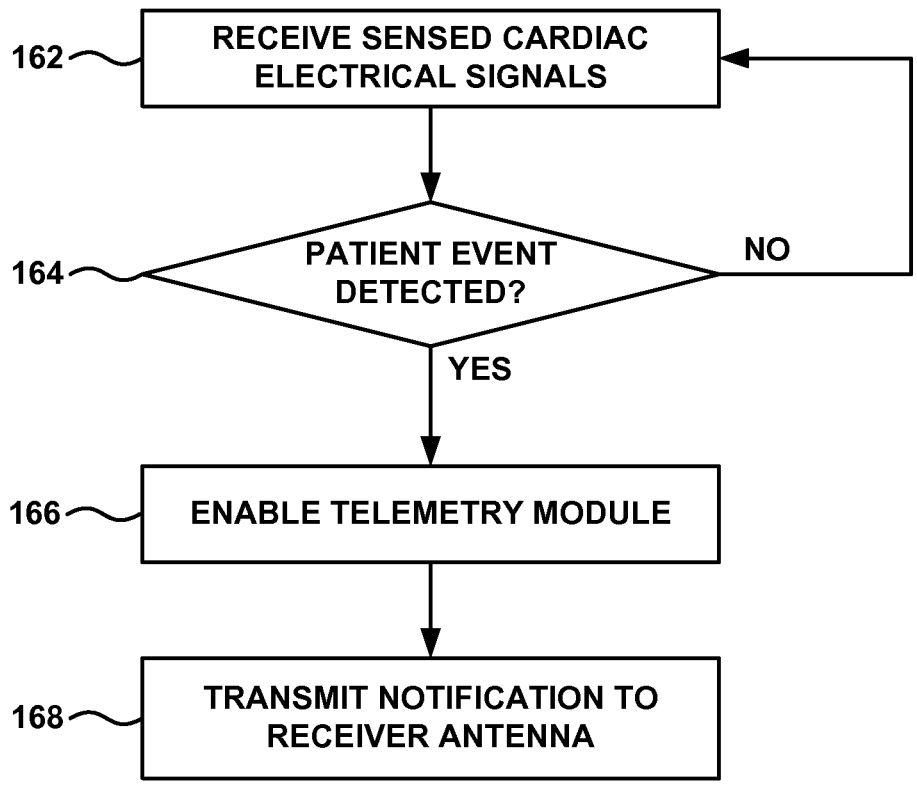
FIG. 9 is a flow diagram of an example technique performed by an IMD for determining whether to enable wireless telemetry during an MRI scan.

FIG. 9 is a flow diagram that illustrates an example of a technique that IMD 16 may implement to determine when to enable wireless telemetry and transmit a notification that patient 14 is experiencing a cardiac arrhythmia. FIG. 9 will be described with concurrent reference to FIG. 6. As described above, IMD 16 may be configured in an MRI-compatible operating mode prior to patient 14 undergoing an MRI scan. For example, processor 120 may be configured to enter an MRI-compatible operating mode based on an indication of an MRI scan to be performed on a patient in which the IMD is implanted. The indication may be provided by a user via programmer 24. Alternatively, the indication may be provided by an MRI sensor that detects an MRI magnetic field. The MRI-compatible mode may include a first mode and a second mode, as described above. In the first mode of the MRI-compatible operating mode, processor 120 may disable telemetry module 128 to reduce electromagnetic fields generated by operation of IMD 16, with the goal of reducing EMI with the MRI scan. Processor 120 may operate IMD 16 in a first mode with telemetry disabled unless the patient event is detected. In some examples, in the first mode of the MRI-compatible operating mode, processor 120 may also at least partially disable therapy delivery module 124, e.g., when therapy delivery module 124 delivers electrical stimulation in the form of defibrillation stimulation. As described above, in some examples, MRI scanner 82 may generate magnetic fields during an MRI scan that saturates a core of a high voltage transformer in IMD 16, which may prevent charging of high voltage capacitors used to store electrical energy for defibrillation stimulation. In the technique of FIG. 9, processor 120 is already configured in the first mode of the MRI-compatible operating mode and the MRI scan has begun. Processor 120 then receives data representing cardiac electrical signals sensed by sensing module 126 via at least two of electrodes 40, 42, 44, 46, 48, 50, 58, 62, 64, 66 (162).

Processor 120 may be configured to detect a patient event (164) based on data generated by a sensing module. The data may be generated based on sensed electrical activity. Although sensing cardiac signals (162) is described in FIGS. 9-11 for purposes of illustration, other physiological or operational conditions may be sensed, in addition or as an alternative to cardiac signals, in order to provide data for detection of a patient event. In the example of FIG. 9, processor 120 may process the sensed cardiac electrical signals according to techniques known in the art to determine whether the cardiac electrical signals indicate a patient event, such as a cardiac arrhythmia (164). For example, processor 120 may use the count in the interval counters described above to detect an arrhythmia event, such as atrial or ventricular fibrillation or an atrial or ventricular tachycardia. In some examples, processor 120 may determine that tachyarrhythmia or fibrillation has occurred by identification of shortened R-R (or P-P) interval lengths. Generally, processor 120 detects tachycardia when the interval length falls below 220 milliseconds (ms) and fibrillation when the interval length falls below 180 ms. These interval lengths are merely examples, and a user may define the interval lengths as desired, which may then be stored within memory 122. This interval length may need to be detected for a certain number of consecutive cycles, for a certain percentage of cycles within a running window, or a running average for a certain number of cardiac cycles, as examples. As described above, in some examples, processor 120 may receive data representative of other physiological parameters, such as intracardiac or intravascular pressure, posture, respiration, or thoracic impedance, and may detect the patient event based on these signals alone or in combination with cardiac electrical signals.

Processor 120 may operate the IMD 16 in a first mode in which the telemetry module 128 is disabled and the therapy delivery module 124 is at least partially disabled when the patient event is not detected. When the patient event is detected (164), processor 120 may operate the IMD in a second mode in which the telemetry module 128 is enabled and the therapy delivery module 124 is at least partially disabled. In the second mode, with telemetry enabled, IMD 16 may transmit a notification of the patient event to receiver antenna 96 (168). In some examples, processor 120 may implement additional decisional criteria in determining whether a patient event has occurred that is sufficient to cause processor 120 to enable telemetry module 128 (166) and transmit a notification of an arrhythmia (168). For example, processor 120 may only enable telemetry module 128 when processor 120 detects a predetermined type of cardiac arrhythmia, such as ventricular fibrillation or ventricular tachycardia. In such examples, processor 120 may not enable telemetry module 120 when processor 120 detects other types of cardiac arrhythmias, such as a bradycardia or an atrial tachycardia or fibrillation.

In some examples, processor 120 may compare the duration of the cardiac arrhythmia (e.g., a count of to a number of consecutive R-R or P-P intervals) to a threshold duration (e.g., a threshold count) and when the cardiac arrhythmia has continued longer than the threshold duration, processor 120 may enable telemetry module 128 (166) and generate and transmit a notification to the wireless telemetry receiver antenna 96 (168). When the duration of the cardiac arrhythmia is less than the threshold duration, processor 120 may continue to sense electrical activity of heart 12 via sensing module 126, but may not enable telemetry module 128.

Processor 120 may compare the rate of the cardiac arrhythmia to a threshold rate (e.g., the R-R or P-P interval duration to a threshold interval duration) and when the rate satisfies a predetermined relationship to the threshold rate, processor 120 may enable telemetry module 128. For example, when processor 120 detects a tachycardia, processor 120 compares the R-R or P-P interval to a threshold R-R or P-P interval. When the interval is less than or equal to the threshold interval, processor 120 may enable telemetry module 128. When the determined interval is greater than the threshold interval, processor 120 may not enable telemetry module 128, but may continue sensing cardiac electrical signals via sensing module 126. In some examples, the threshold interval may be equal to the interval at which processor 120 categorizes the cardiac electrical signal as indicating a tachycardia (e.g., 220 ms). In other examples, the threshold interval may be equal to a different value (e.g., between 220 ms and 180 ms).

In some examples, processor 120 may implement two or more of the decisional criterion described above, in any combination. For example, processor 120 may compare the interval determined from the cardiac electrical activity to a threshold interval and may compare a duration of the cardiac arrhythmia to a threshold duration when determining whether to enable telemetry module 128. Other combinations are also possible and within the scope of this disclosure.

When processor 120 determines that the signals sensed by sensing module 126 do not indicate that patient 14 is experiencing a cardiac arrhythmia ("NO" branch of decision block 164), processor 120 continues to receive sensed cardiac electrical signals from sensing module 126 (162) and analyzes the signals to determine if the signals indicate a patient event (164).

When processor 120 determines that patient 14 is experiencing an arrhythmia (164) or is experiencing a type of arrhythmia that is to be communicated to a user, processor 120 enables telemetry module 128 (166). In some examples, processor 120 may enable telemetry module 128 by causing a hardware switch to close and connect telemetry module 128 processor 120. In other examples, processor 120 may enable telemetry module 128 by changing a state in software or firmware that causes telemetry module 128 to be functional.

Once processor 120 has enabled telemetry module 128 (166), processor 120 may generate and transmit a notification of the cardiac arrhythmia to wireless telemetry receiver antenna 96 (168). In some examples, processor 120 may generate and transmit the notification of the patient event upon entering the second operating mode. Processor 120 may, in some examples, automatically transmit the notification to wireless telemetry receiver antenna 96, e.g., without first being interrogated by an external device, such as programmer 24, display device 102, or MRI control console 86. In other examples, processor 120 may generate the notification, but may not transmit the notification until processor 120 is interrogated by the external device, e.g., programmer 24, display device 102, or MRI control console 86. In some examples, the external device may be configured to periodically interrogate processor 120, e.g., at a time when the interrogation may not undesirably interfere with the MRI scan. For example, the external device may interrogate processor 120 at times while MRI scanner 82 is not actively performing a scan of patient 14.

As described above, in some examples, the notification that processor 120 generates and transmits may be relatively simple and may include an indication that patient 14 is experiencing a cardiac arrhythmia and an indication of the type of cardiac arrhythmia that the patient 14 is experiencing. For example, the notification may include a label such as bradycardia, atrial or ventricular tachycardia, or atrial or ventricular fibrillation.

In some examples, the notification that processor 120 generates and transmits may include additional or alternative information. For example, the notification may include data such as EGM data representative of the sensed cardiac electrical activity based on which processor 120 determined patient 14 was experiencing a cardiac arrhythmia, a calculated heart rate of patient 14, marker channel data indicating cardiac events, rating information that indicates a severity of the patient event, information regarding an operating mode of IMD 16, other operating parameters of IMD 16, or the like.

In the example of FIG. 9, detection of patient events based on sensed cardiac electrical signals is described. Additionally, or alternatively, processor 120 may be configured to receive other types of sensed data and determine whether a patient event is detected based on such data. For example, IMD 16 may sense any of a variety of physiological conditions, such as a cardiac arrhythmia, asystole, intracardiac or intravascular pressure, posture, respiration, mechanical motion of heart 12, tissue perfusion, or thoracic impedance, or other parameters, in addition to or as an alternative to sensed cardiac electrical activity of heart 12. Such additional or alternative parameters may be sensed by any of a variety of suitable sensors, such as accelerometers, pressure sensors, optical sensors, electrodes, or the like.

As discussed above, IMD 16 also may detect a patient event based on events associated with operational status of the IMD, such as an operating mode of the IMD, capture or loss of capture of tissue when delivering electrical stimulation, a magnetic field sensed by a sensor of the IMD, IMD battery status, lead or electrical conductor conditions, or sensor operating status. For example, IMD 16 may detect a patient event when an operating mode of the IMD changes, when a battery charge drops below a prescribed level, when a magnetic field sensor changes state or indicates a magnetic field that exceeds or drops below a threshold, when lead or electrical conductor characteristics such as impedance exceed or drop below a threshold, or when a prescribed sensor operating status (e.g., enabled or disabled) changes.

Figure 10:
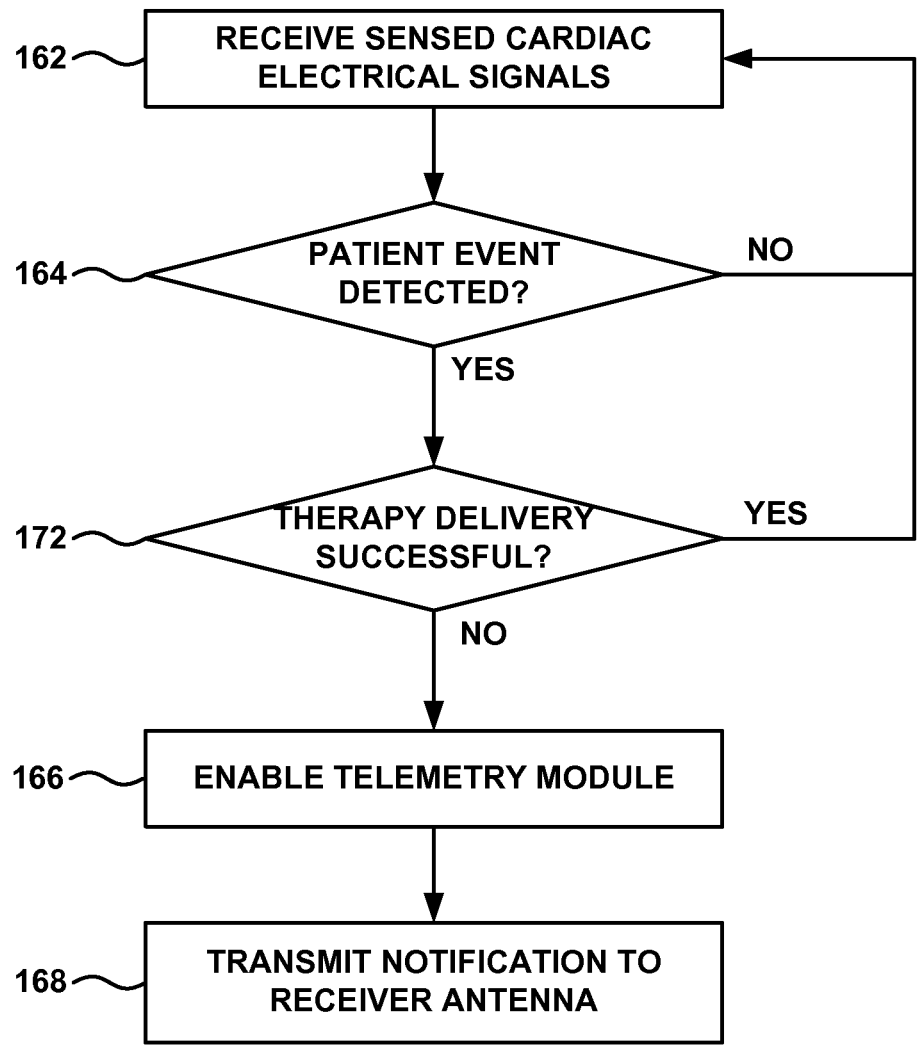
FIG. 10 is another flow diagram of an example technique performed by an IMD for determining whether to enable wireless telemetry during an MRI scan.

FIG. 10 is another flow diagram that illustrates an example of a technique that IMD 16 may implement to determine when to enable wireless telemetry and transmit a notification that patient 14 is experiencing a cardiac arrhythmia. Similar to FIG. 9, in the technique of FIG. 10, processor 120 is already configured in the first mode of the MRI-compatible operating mode and the MRI scan has begun. Processor 120 then receives data representing cardiac electrical signals sensed by sensing module 126 via at least two of electrodes 40, 42, 44, 46, 48, 50, 58, 62, 64, 66 (162), and analyzes the data to determine whether a patient event has occurred (164).

In the technique illustrated in FIG. 10, once processor 120 detects a patient event (the "YES" branch of decision block 164), processor 120 may control therapy delivery module 124 to deliver electrical stimulation therapy to heart 12, and may determine whether therapy delivery by therapy delivery module 124 was successful (172). As described above, in some examples, MRI scanner 82 (FIGS. 3-5) may produce magnetic fields that saturate a transformer core of a high voltage transformer in IMD 16 which converts the voltage output by power source 130 to a voltage suitable for charging high voltage capacitors used to deliver electrical stimulation therapy, such as defibrillation stimulation therapy. Accordingly, in examples in which IMD 16 is located within a magnetic field of sufficient intensity, therapy delivery module 124 may not be able to cause the high voltage capacitors to charge and may not be able to deliver stimulation therapy to heart 12. In such examples, processor 120 may determine that therapy delivery module 124 cannot deliver stimulation therapy to heart 12 (the "NO" branch of decision block 172), and may enter the second mode of the MRI-compatible operating mode. Processor 120 may then enable telemetry module 128 (166) and generate and transmit a notification of the patient event to wireless telemetry receiver antenna 96 via telemetry module 128 (168).

When processor 120 detects a patient event (164) and controls therapy delivery module 124 to attempt to deliver electrical stimulation therapy to heart 12, therapy delivery module 124 may be able to successfully delivery electrical stimulation to heart 12 (the "YES" branch of decision block 172). For example, the MRI scanner 82 may not at that time be generating a magnetic field that saturates the transformer core, or the MRI scan may be complete. In some examples, as illustrated in FIG. 10, processor 120 may return to receiving sensed cardiac electrical signals from sensing module 126 (162) upon determining that therapy delivery module 124 has successfully delivered electrical stimulation therapy to heart 12. In other examples, although not shown in FIG. 10, upon determining that therapy delivery module 124 has successfully delivered electrical stimulation therapy to heart 12, processor 120 may enter the second mode, enable telemetry module 128 (166) and transmit a notification of the patient event to wireless telemetry receiver antenna 96 via telemetry module 128 (168).

Figure 11:
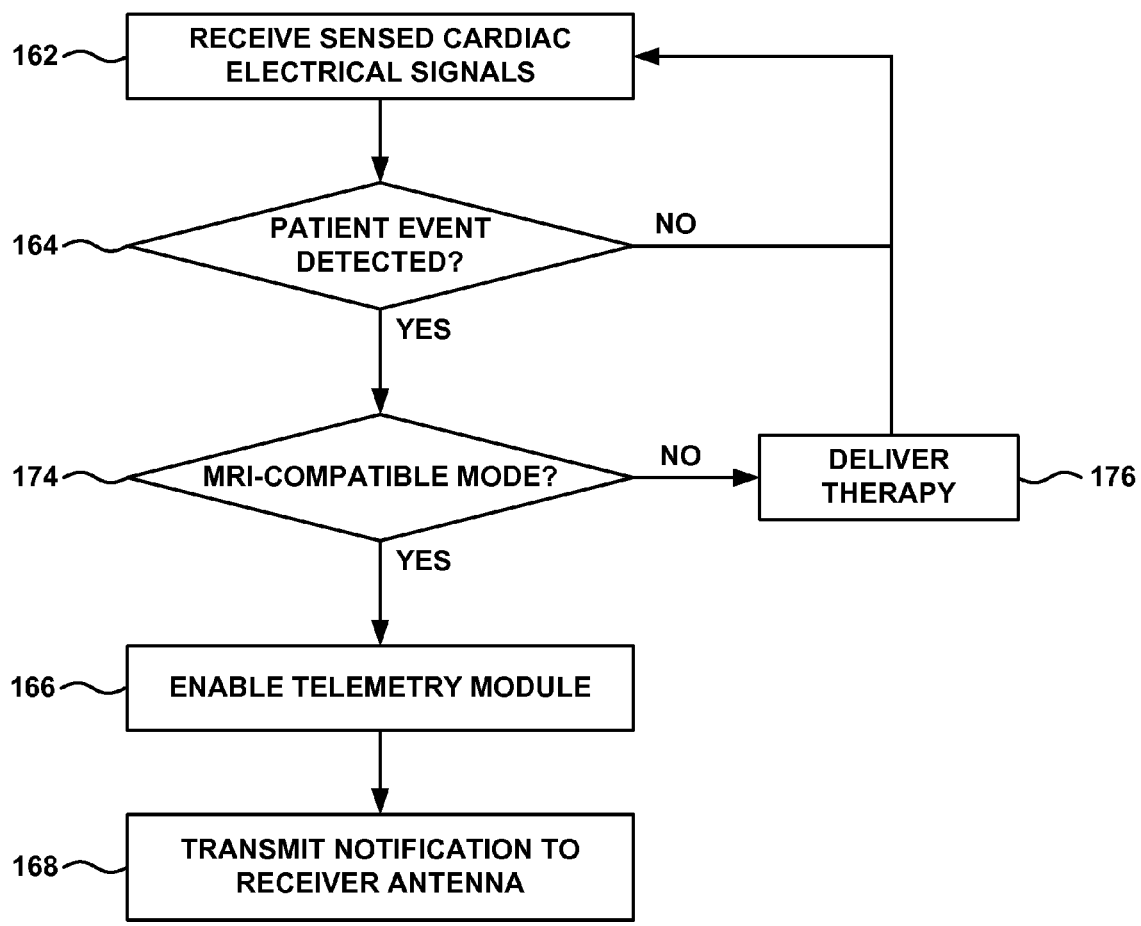
FIG. 11 is another flow diagram of an example technique performed by an IMD for determining whether to enable wireless telemetry during an MRI scan.

FIG. 11 is another flow diagram that illustrates an example of a technique that IMD 16 may implement to determine when to enable wireless telemetry and transmit a notification that patient 14 is experiencing a cardiac arrhythmia. Similar to FIGS. 9 and 10, in the technique of FIG. 11, processor 120 is already configured in the first mode of the MRI-compatible operating mode and the MRI scan has begun. Processor 120 then receives data representing cardiac electrical signals sensed by sensing module 126 via at least two of electrodes 40, 42, 44, 46, 48, 50, 58, 62, 64, 66 (162), and analyzes the data to determine whether a patient event has occurred (164).

Once processor 120 detects a patient event (the "YES" branch of decision block 164), processor 120 may determine if processor 120 is operating in the MRI-compatible operating mode or is operating in a standard operating mode (174). When processor 120 determines it is operating in the standard operating mode (the "NO" branch of decision block 174), processor 120 may control therapy module 124 to deliver electrical stimulation therapy to patient 14 (176). In some examples, as illustrated in FIG. 11, processor 120 may return to receiving sensed cardiac electrical signals from sensing module 126 (162) upon controlling therapy delivery module 124 to deliver electrical stimulation therapy to heart 12. In other examples, although not shown in FIG. 11, upon controlling therapy delivery module 124 to deliver electrical stimulation therapy to heart 12, processor 120 may enter the second mode, enable telemetry module 128 (166) and transmit a notification of the patient event to wireless telemetry receiver antenna 96 via telemetry module 128 (168).

When processor 120 determines it is operating in the MRI compatible operating mode (the "YES" branch of decision block 174), processor 120 may enable the second mode of the MRI compatible operating mode. Processor 120 then enables telemetry module 128 (166) and transmits a notification of the patient event to wireless telemetry receiver antenna 96 via telemetry module 128 (168).

The techniques described in this disclosure may be applicable to IMDs that support sensing and delivery of therapy. In other examples, the techniques may be applicable to IMDs that provide sensing only. For example, if IMD 16 forms a sensing or monitoring device, in an MRI-compatible mode, processor 120 may operate the IMD in a first mode in which the telemetry module 128 is disabled when the patient event is not detected. When a patient event is detected, processor 120 may operate IMD 16 in a second mode in which the telemetry module 128 is enabled. In the second mode, with telemetry enabled, IMD 16 may transmit a notification of the patient event to receiver antenna 96.

The techniques described in this disclosure, including those attributed to IMD 16, programmer 24, MRI control console 86, display device 102, or other devices or elements such as modules, units or components of such devices, may be implemented, at least in part, in hardware, software, firmware or any combination thereof. Even where functionality may be implemented in part by software or firmware, such elements will be implemented in a hardware device. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a non-transitory computer-readable medium such as RAM, ROM, NVRAM, EEPROM, FLASH memory, magnetic data storage media, optical data storage media, or the like. The instructions may be executed to support one or more aspects of the functionality described in this disclosure.

Additionally, while the examples described herein primarily focus on an IMD that senses activity of a heart and selectively provides notification to an external device if the IMD detects a cardiac arrhythmia, the techniques described herein may be implemented in other IMDs, and for other patient events. For example, the techniques may be implemented in a neurostimulator that delivers, for example, spinal cord stimulation, deep brain stimulation, peripheral nerve stimulation, pelvic floor stimulation, gastric stimulation, or the like. In examples in which the techniques described herein are implemented in a neurostimulator, the patient event may be, for example, a seizure or other condition relating to neurological function.

Various examples have been described. These and other examples are within the scope of the following claims.

The invention claimed is:

1. An implantable medical device (IMD) comprising:
a telemetry module;
a sensing module;
a therapy delivery module; and
a processor configured to:
   detect a patient event based on data generated by the sensing module,
   operate the IMD in a first mode in which the telemetry module is disabled and the therapy delivery module is at least partially disabled when the patient event is not detected, and
   operate the IMD in a second mode in which the telemetry module is enabled and the therapy delivery module is at least partially disabled when the patient event is detected,
   wherein the processor is configured to enter a magnetic resonance imaging (MRI)-compatible operating mode based on an indication of an MRI scan to be performed on a patient in which the IMD is implanted, and wherein, in the MRI-compatible operating mode, the processor operates the IMD in the first mode unless the patient event is detected.

2. The IMD of claim 1, wherein the sensing module is configured to sense electrical activity of a heart of the patient and generate the data based on the sensed electrical activity, and wherein the patient event comprises a cardiac arrhythmia.

3. The IMD of claim 2, wherein the processor is configured to, in the second mode, generate a notification of the cardiac arrhythmia and transmit the notification to an external device via the telemetry module.

4. The IMD of claim 3, wherein the notification comprises at least one of an indication of a cardiac arrhythmia, an indication of a type of the cardiac arrhythmia, or data representing a cardiac electrical signal.

5. The IMD of claim 3, wherein the processor is configured to operate the IMD in the second mode only when the cardiac arrhythmia comprises a ventricular tachycardia or a ventricular fibrillation.

6. The IMD of claim 1, wherein the telemetry module is configured to receive a wireless communication from an external programmer device and the processor is configured to enter into the MRI-compatible operating mode in response to the wireless communication.

7. The IMD of claim 1, further comprising a sensor configured to detect a magnetic field associated with an MRI device, the processor is configured to enter into the MRI-compatible operating mode in response to the sensor detecting the magnetic field associated with the MRI device.

8. A system comprising:
a wireless telemetry receiver antenna located within an electromagnetic interference (EMI)-shielded room;
an external device communicatively coupled to the wireless telemetry receiver antenna via a wired connection; and
an implantable medical device (IMD) comprising a telemetry module, a sensing module, a therapy delivery module, and a processor, wherein the processor is configured to:
   detect a patient event based on data generated by the sensing module,
   operate the IMD in a first mode in which the telemetry module is disabled and the therapy delivery module is at least partially disabled when the patient event is not detected,
   operate the IMD in a second mode in which the telemetry module is enabled and the therapy delivery module is at least partially disabled when the patient event is detected,
   generate a notification of the detected patient event, and
   transmit the notification to the external device via the telemetry module of the IMD and the wireless telemetry receiver antenna,
   wherein the EMI-shielded room encloses a magnetic resonance imaging (MRI) scanner, wherein the processor of the IMD is configured to enter an MRI-compatible operating mode based on an indication of an MRI scan to be performed on the patient, and wherein, in the MRI-compatible operating mode, the processor operates the IMD in the first mode unless the patient event is detected.

9. The system of claim 8, wherein the external device comprises a programmer for the IMD.

10. The system of claim 8, wherein the external device comprises a display device that displays information based on the notification.

11. The system of claim 8, wherein the external device comprises a magnetic resonance imaging control console.

12. The system of claim 8, wherein the external device is located outside of the electromagnetic interference-shielded room.

13. The system of claim 12, wherein the wireless telemetry receiver antenna is communicatively coupled to the external device via at least one of an optical waveguide, an electrical cable, or an infrared wireless communication link.

14. The system of claim 8, wherein the external device is located within the electromagnetic interference-shielded room, and wherein the external device is configured to communicate the notification of the cardiac arrhythmia to a user located outside of the electromagnetic interference-shielded room.

15. The system of claim 8, wherein the sensing module of the IMD is configured to sense electrical activity of a heart of the patient and generate the data based on the sensed electrical activity, and wherein the patient event comprises a cardiac arrhythmia.

16. The system of claim 15, wherein the notification comprises at least one of an indication of an arrhythmia, an indication of a type of cardiac arrhythmia, or data representing a cardiac electrical signal.

17. The system of claim 15, wherein the processor is configured to operate the IMD in the second mode only when the cardiac arrhythmia comprises a ventricular tachycardia or a ventricular fibrillation.

18. The system of claim 8, wherein the external device is configured to communicate the notification to a user via at least one of a visual alert or an audible alert.

19. A method comprising:
detecting a patient event based on data generated by a sensing module of an implantable medical device (IMD) in a patient;
operating the IMD in a first mode in which a telemetry module of the IMD is disabled and a therapy delivery module of the IMD is at least partially disabled when the patient event is not detected;

operating the IMD in a second mode in which the telemetry module is enabled and the therapy delivery module is at least partially disabled when the patient event is detected; and operating the IMD in a magnetic resonance imaging (MRI)-compatible operating mode based on an indication of an MRI scan to be performed on a patient in which the IMD is implanted, wherein, in the MRI-compatible operating mode, the IMD operates in the first mode unless the patient event is detected.

20. The method of claim 19, further comprising:
generating a notification based on the detected patient event; and
transmitting the notification via the telemetry module to an external device while operating the IMD in the second mode.

21. The method of claim 20, wherein the external device comprises at least one of a programmer for the IMD, a display device, or an MRI control console.

22. The method of claim 20, wherein the external device is located within an EMI-shielded room in which the MRI scan is performed.

23. The method of claim 20, wherein the external device is located outside of an EMI-shielded room in which the MRI scan is performed.

24. The method of claim 23, wherein the device is communicatively coupled to a wireless telemetry receiver antenna located in the EMI shielded room via at least one of an optical waveguide, an electrical cable, or an infrared wireless communication link.

25. The method of claim 20, further comprising communicating the notification to a user located outside an EMI-shielded room via the external device.

26. The method of claim 25, wherein communicating the notification to the user via the external device comprises communicating at least one of visual notification or an audible notification to the user.

27. The method of claim 20, wherein detecting the patient event based on data generated by the sensing module of the IMD comprises detecting a cardiac arrhythmia.

28. The method of claim 20, further comprising detecting the patient event during the MRI scan performed on the patient.

29. The method of claim 20, wherein the notification comprises at least one of an indication of a cardiac arrhythmia, an indication of a type of the cardiac arrhythmia, or data representing a cardiac electrical signal.

30. The method of claim 19, wherein detecting the patient event based on data generated by the sensing module of the IMD comprises detecting a ventricular tachycardia or ventricular fibrillation.

31. A non-transitory computer readable medium comprising instructions that cause a programmable processor to:
detect a patient event based on data generated by a sensing module of an implantable medical device (IMD) in a patient;
operate the IMD in a first mode in which a telemetry module of the IMD is disabled and a therapy delivery module of the IMD is at least partially disabled when the patient event is not detected;
operate the IMD in a second mode in which the telemetry module is enabled and the therapy delivery module is at least partially disabled when the patient event is detected; and
operate the IMD in a magnetic resonance imaging (MRI)-compatible operating mode based on an indication of an MRI scan to be performed on a patient in which the IMD is implanted, wherein, in the MRI-compatible operating mode, the IMD operates in the first mode unless the patient event is detected.

32. An implantable medical device (IMD) comprising:
means for detecting a patient event based on data generated by a sensing module of an implantable medical device (IMD) in a patient;
means for operating the IMD in a first mode in which a telemetry module of the IMD is disabled and a therapy delivery module of the IMD is at least partially disabled when the patient event is not detected;
means for operating the IMD in a second mode in which the telemetry module is enabled and the therapy delivery module is at least partially disabled when the patient event is detected; and
means for operating the IMD in a magnetic resonance imaging (MRI)-compatible operating mode based on an indication of an MRI scan to be performed on a patient in which the IMD is implanted, wherein, in the MRI-compatible operating mode, the IMD operates in the first mode unless the patient event is detected.

* * * * *